(12) United States Patent
Cohen et al.

(10) Patent No.: US 10,869,692 B2
(45) Date of Patent: Dec. 22, 2020

(54) TOOLS AND METHODS FOR VAGINAL ACCESS

(71) Applicant: Memic Innovative Surgery Ltd., Or-Yehuda (IL)

(72) Inventors: Dvir Cohen, Ramot-Menashe (IL); Yaron Levinson, Tel-Aviv (IL); Eyal Maimon, Kfar Edumim (IL); Idan Rotem, Tel Aviv (IL)

(73) Assignee: Memic Innovative Surgery Ltd., Or-Yehuda (IL)

( * ) Notice: Subject to any disclaimer, the term of this patent is extended or adjusted under 35 U.S.C. 154(b) by 0 days.

(21) Appl. No.: 16/109,879

(22) Filed: Aug. 23, 2018

(65) Prior Publication Data
US 2019/0059868 A1 Feb. 28, 2019

Related U.S. Application Data

(60) Provisional application No. 62/549,078, filed on Aug. 23, 2017, provisional application No. 62/549,097, (Continued)

(51) Int. Cl.
*A61B 17/34* (2006.01)
*A61B 17/00* (2006.01)
(Continued)

(52) U.S. Cl.
CPC ...... *A61B 17/3423* (2013.01); *A61B 1/00137* (2013.01); *A61B 1/00154* (2013.01);
(Continued)

(58) Field of Classification Search
CPC ........... A61B 90/50; A61B 90/06; A61B 1/01; A61B 1/00147–0016;
(Continued)

(56) References Cited

U.S. PATENT DOCUMENTS 5,540,675 A * 7/1996 Hasson .............. A61B 17/3403
606/1
5,762,629 A 6/1998 Kambin
(Continued)

FOREIGN PATENT DOCUMENTS

WO WO 2019/038770 2/2019

OTHER PUBLICATIONS

International Search Report and the Written Opinion dated Feb. 4, 2019 From the International Searching Authority Re. Application No. PCT/IL2018/050934. (20 Pages).
(Continued)

*Primary Examiner* — Ellen C Hammond

(57) ABSTRACT

Trocar components and methods of use are described, wherein the trocar components are configured to provide access to intraperitoneal space via the rectouterine pouch to surgical tools, which optionally include one or more surgical robot members. The surgical tools are optionally 5 mm or more in diameter. In some embodiments, a cannula part has a lumen sized to provide to a plurality of the surgical tools simultaneous transvaginal access to the intraperitoneal space via the rectouterine pouch. In some embodiments, an incision sized to receive a distal aperture of the cannula is created, optionally using one or two dilators. The dilators are sized to create (optionally starting from a puncture by a needle 2 mm in diameter or less) an oblong aperture. In some embodiments, the oblong aperture is at least twice as wide across a long diameter as across a short diameter.

23 Claims, 20 Drawing Sheets

Related U.S. Application Data filed on Aug. 23, 2017, provisional application No. 62/558,460, filed on Sep. 14, 2017, provisional application No. 62/558,469, filed on Sep. 14, 2017.

(51) Int. Cl.

| | | |
|---|---|---|
| *A61M 29/02* | (2006.01) | |
| *A61B 34/30* | (2016.01) | |
| *A61B 1/313* | (2006.01) | |
| *A61B 1/00* | (2006.01) | |
| *A61B 1/01* | (2006.01) | |
| *A61B 17/02* | (2006.01) | |
| *A61B 17/42* | (2006.01) | |
| *A61M 29/00* | (2006.01) | |
| A61B 90/00 | (2016.01) | |
| A61B 90/50 | (2016.01) | |

(52) U.S. Cl.
CPC ............... *A61B 1/01* (2013.01); *A61B 1/313* (2013.01); *A61B 17/00234* (2013.01); *A61B 17/0218* (2013.01); *A61B 17/3421* (2013.01); *A61B 17/3494* (2013.01); *A61B 17/3496* (2013.01); *A61B 17/4241* (2013.01); *A61B 34/30* (2016.02); *A61M 29/00* (2013.01); *A61M 29/02* (2013.01); *A61B 17/3417* (2013.01); *A61B 17/42* (2013.01); *A61B 90/50* (2016.02); *A61B 2017/0042* (2013.01); *A61B 2017/00278* (2013.01); *A61B 2017/00398* (2013.01); *A61B 2017/00991* (2013.01); *A61B 2017/345* (2013.01); *A61B 2017/3443* (2013.01); *A61B 2017/3445* (2013.01); *A61B 2017/3452* (2013.01); *A61B 2017/3456* (2013.01); *A61B 2017/3466* (2013.01); *A61B 2017/4216* (2013.01); *A61B 2034/301* (2016.02); *A61B 2034/302* (2016.02); *A61B 2090/061* (2016.02)

(58) Field of Classification Search
CPC .......... A61B 17/34–3498; A61B 17/02–0293; A61B 17/17–01796; A61B 34/30
See application file for complete search history.

(56) References Cited

U.S. PATENT DOCUMENTS

| | | | | |
|---|---|---|---|---|
| 5,797,835 | A * | 8/1998 | Green | A61B 17/3401 |
| | | | | 600/106 |
| 5,882,344 | A | 3/1999 | Stouder, Jr. | |
| 6,156,006 | A | 12/2000 | Brosens et al. | |
| 7,927,271 | B2 | 4/2011 | Dimitriou et al. | |
| 8,608,652 | B2 | 12/2013 | Voegele et al. | |
| 8,926,532 | B2 * | 1/2015 | Barrett | A61B 5/1071 |
| | | | | 33/511 |
| 2004/0176763 | A1 * | 9/2004 | Foley | A61M 29/02 |
| | | | | 606/60 |
| 2004/0181231 | A1 | 9/2004 | Emstad et al. | |
| 2004/0260246 | A1 | 12/2004 | Desmond | |
| 2006/0069383 | A1 * | 3/2006 | Bogaerts | A61B 90/40 |
| | | | | 606/1 |
| 2007/0118119 | A1 | 5/2007 | Hestad | |
| 2008/0064921 | A1 * | 3/2008 | Larkin | A61B 1/00154 |
| | | | | 600/104 |
| 2008/0086150 | A1 * | 4/2008 | Mathis | A61B 90/50 |
| | | | | 606/130 |
| 2008/0228213 | A1 | 9/2008 | Blakeney et al. | |
| 2009/0084216 | A1 * | 4/2009 | Schena | A61B 34/71 |
| | | | | 74/490.06 |
| 2009/0192520 | A1 * | 7/2009 | Finlay | A61B 90/50 |
| | | | | 606/130 |
| 2009/0264899 | A1 * | 10/2009 | Appenrodt | A61N 1/0529 |
| | | | | 606/130 |
| 2010/0249525 | A1 | 9/2010 | Shelton, IV et al. | |
| 2010/0268241 | A1 | 10/2010 | Horn et al. | |
| 2011/0105850 | A1 | 5/2011 | Voegele et al. | |
| 2011/0277775 | A1 * | 11/2011 | Holop | A61B 34/35 |
| | | | | 128/849 |
| 2012/0130187 | A1 | 5/2012 | Okoniewski | |
| 2012/0165611 | A1 | 6/2012 | Warren et al. | |
| 2012/0182134 | A1 * | 7/2012 | Doyle | A61B 34/30 |
| | | | | 340/12.22 |
| 2013/0053777 | A1 | 2/2013 | Shelton, IV | |
| 2013/0245381 | A1 * | 9/2013 | Dang | A61B 17/3431 |
| | | | | 600/208 |
| 2014/0039267 | A1 * | 2/2014 | Seex | A61B 90/06 |
| | | | | 600/206 |
| 2014/0158141 | A1 | 6/2014 | Winer | |
| 2014/0180308 | A1 * | 6/2014 | von Grunberg | A61B 90/11 |
| | | | | 606/130 |
| 2014/0316209 | A1 | 10/2014 | Overes et al. | |
| 2015/0011978 | A1 | 1/2015 | Okamura et al. | |
| 2015/0196365 | A1 * | 7/2015 | Kostrzewski | A61B 34/30 |
| | | | | 606/130 |
| 2015/0209073 | A1 | 7/2015 | Ahn | |
| 2015/0250992 | A1 | 9/2015 | Morriss et al. | |
| 2016/0008027 | A1 | 1/2016 | Ibrahim et al. | |
| 2016/0199094 | A1 | 7/2016 | Ling et al. | |
| 2017/0027607 | A1 * | 2/2017 | Verbeek | A61B 17/0218 |
| 2017/0056064 | A1 | 3/2017 | Zergiebel et al. | |
| 2017/0065269 | A1 * | 3/2017 | Thommen | A61B 1/07 |
| 2017/0071685 | A1 * | 3/2017 | Crawford | A61B 34/20 |
| 2017/0143435 | A1 * | 5/2017 | Scholan | H01L 27/11582 |
| 2017/0265947 | A1 * | 9/2017 | Dyer | G16H 40/63 |
| 2017/0354470 | A1 * | 12/2017 | Farritor | A61B 1/008 |
| 2018/0049824 | A1 * | 2/2018 | Harris | A61B 34/35 |
| 2018/0070802 | A1 * | 3/2018 | Becerra | A61B 1/00154 |
| 2018/0116741 | A1 * | 5/2018 | Garcia Kilroy | B25J 15/0019 |
| 2018/0140377 | A1 * | 5/2018 | Reichenbach | A61B 34/73 |
| 2018/0153537 | A1 | 6/2018 | Wang et al. | |
| 2018/0199961 | A1 | 7/2018 | Prior et al. | |
| 2018/0243048 | A1 * | 8/2018 | Shan | A61B 8/466 |
| 2018/0318020 | A1 * | 11/2018 | Thompson | A61B 34/30 |
| 2018/0344415 | A1 * | 12/2018 | Yeung | A61B 34/30 |
| 2019/0059939 | A1 | 2/2019 | Cohen et al. | |
| 2019/0059940 | A1 * | 2/2019 | Cohen | A61B 34/30 |
| 2019/0059941 | A1 | 2/2019 | Cohen et al. | |
| 2019/0125480 | A1 * | 5/2019 | Bernstein | A61B 34/30 |
| 2019/0231460 | A1 * | 8/2019 | DiMaio | A61B 17/3423 |
| 2019/0254647 | A1 | 8/2019 | Prior | |
| 2019/0274665 | A1 * | 9/2019 | Garcia | A61B 17/28 |
| 2019/0290389 | A1 * | 9/2019 | Kopp | A61B 90/50 |
| 2019/0321115 | A1 * | 10/2019 | Anderson | A61B 5/062 |
| 2020/0060724 | A1 * | 2/2020 | Abboud | A61B 1/01 |
| 2020/0085530 | A1 * | 3/2020 | Sauer | A61B 17/3423 |
| 2020/0093546 | A1 * | 3/2020 | Ando | A61B 90/90 |

OTHER PUBLICATIONS

Applied Medical Resources Corp. "Alexis® Wound Protectors/Retractors", Applied Medical Resources Corporation, Brochure, 16 P., 2016.
Applied Medical Resources Corp. "GelPOINT® Advanced Access Platforms", Applied Medical Resources Corporation, Brochure, 6 P., 2017.
Official Action dated Nov. 27, 2019 From the US Patent and Trademark Office Re. U.S. Appl. No. 16/109,893. (29 pages).
Restriction Official Action dated Nov. 27, 2019 From the US Patent and Trademark Office Re. U.S. Appl. No. 16/109,880. (5 pages).
International Preliminary Report on Patentability dated Mar. 5, 2020 From the International Bureau of WIPO Re. Application No. PCT/IL2018/050934. (12 pages).
Restriction Official Action dated Mar. 6, 2020 From the US Patent and Trademark Office Re. U.S. Appl. No. 16/109,891. (6 pages).
Notice of Allowance dated Apr. 9, 2020 from the US Patent and Trademark Office Re. U.S. Appl. No. 16/109,893. (11 pages).

(56) References Cited

OTHER PUBLICATIONS

Kondo et al. "Transvaginal Natural Orifice Transluminal Endoscopic Surgery (Notes): Surgical Technique and Results," in: Advanced Gynecologic Endoscopy, Ed: Darwish. Chapter 8, 113-138, 2011.
Official Action dated Apr. 22, 2020 from the US Patent and Trademark Office Re. U.S. Appl. No. 16/109,880. (23 pages).
Official Action dated Aug. 3, 2020 from the US Patent and Trademark Office Re. U.S. Appl. No. 16/109,891. (33 pages).

* cited by examiner

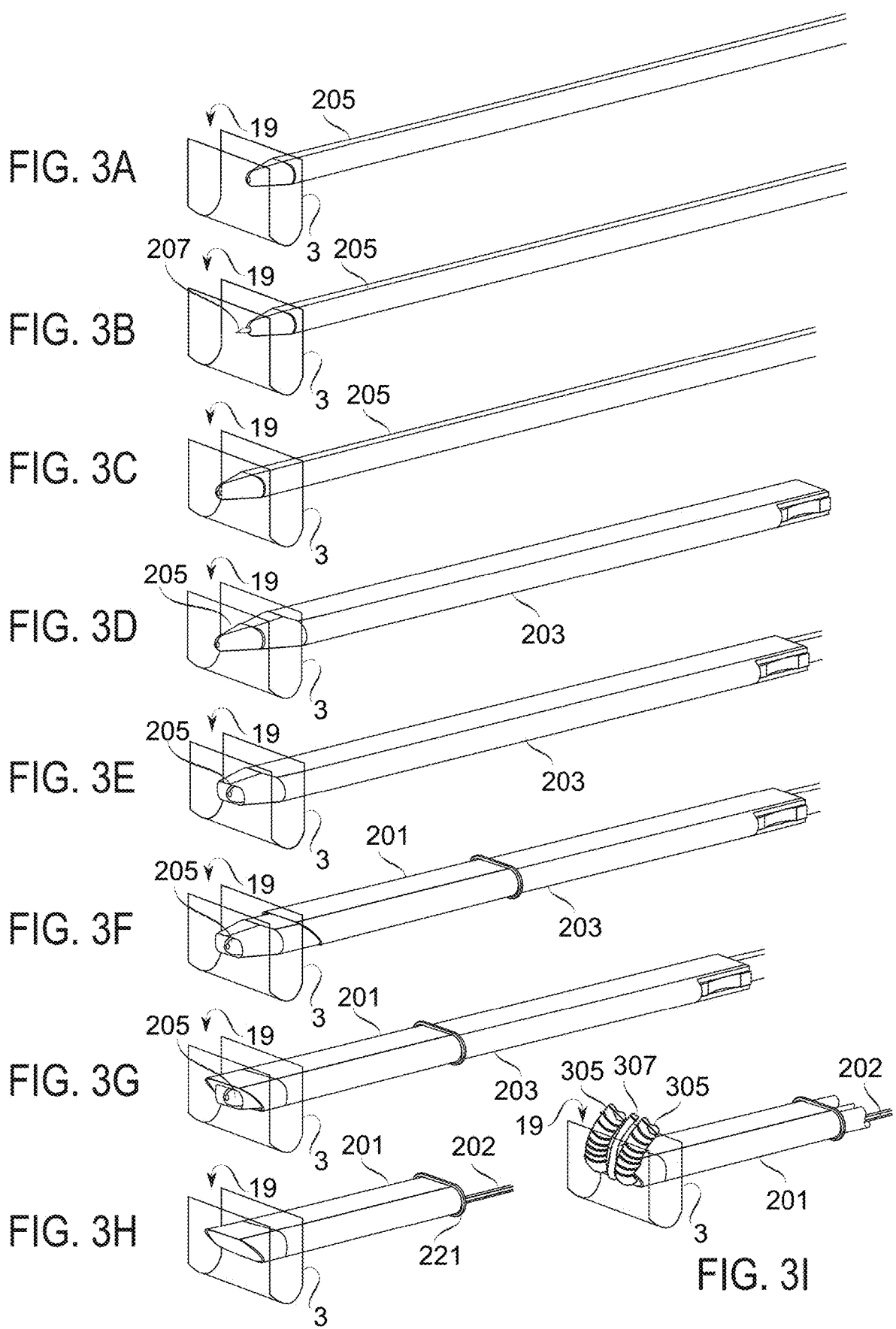

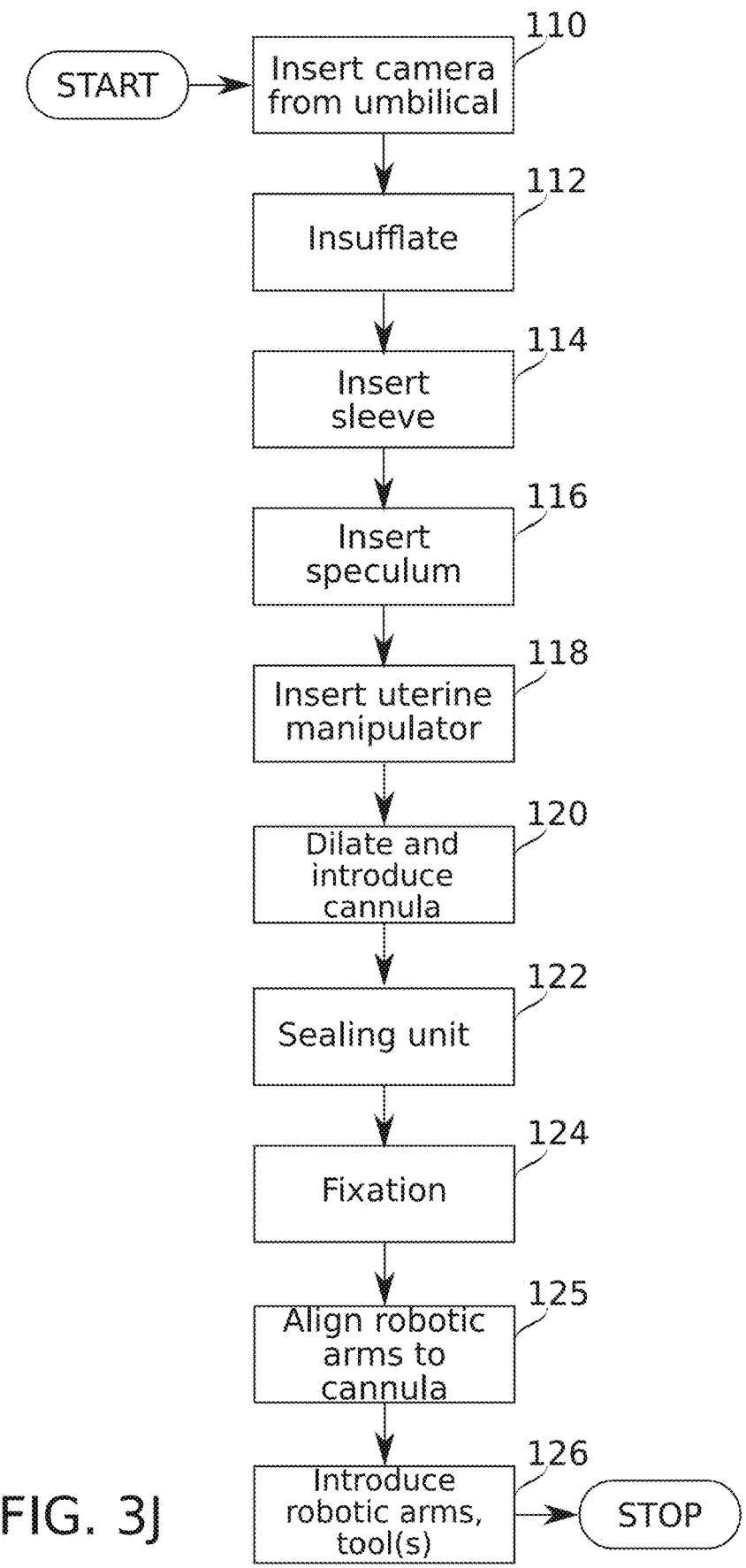

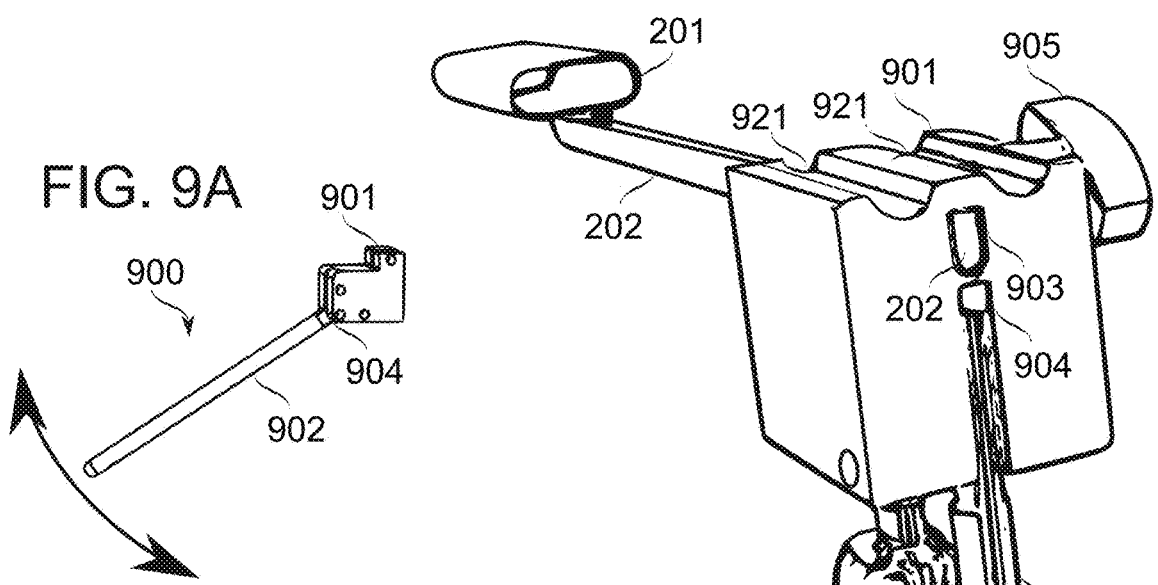
FIG. 9A
FIG. 9B
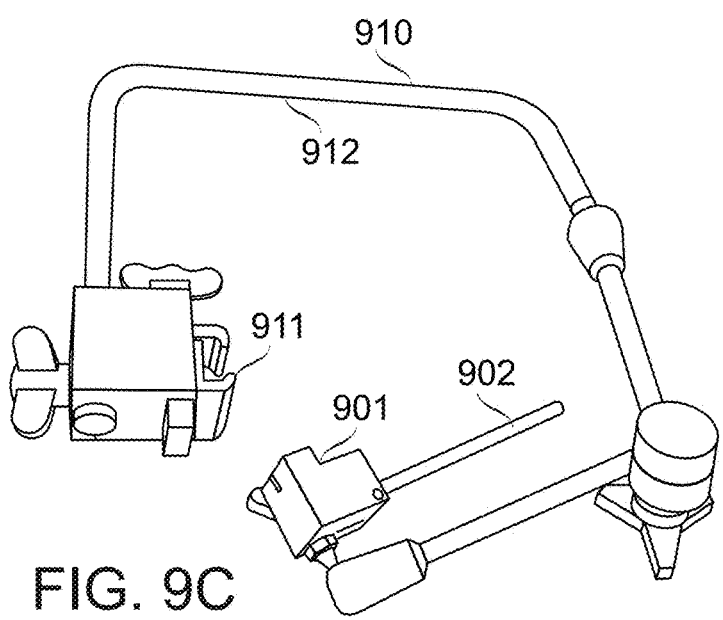
FIG. 9C
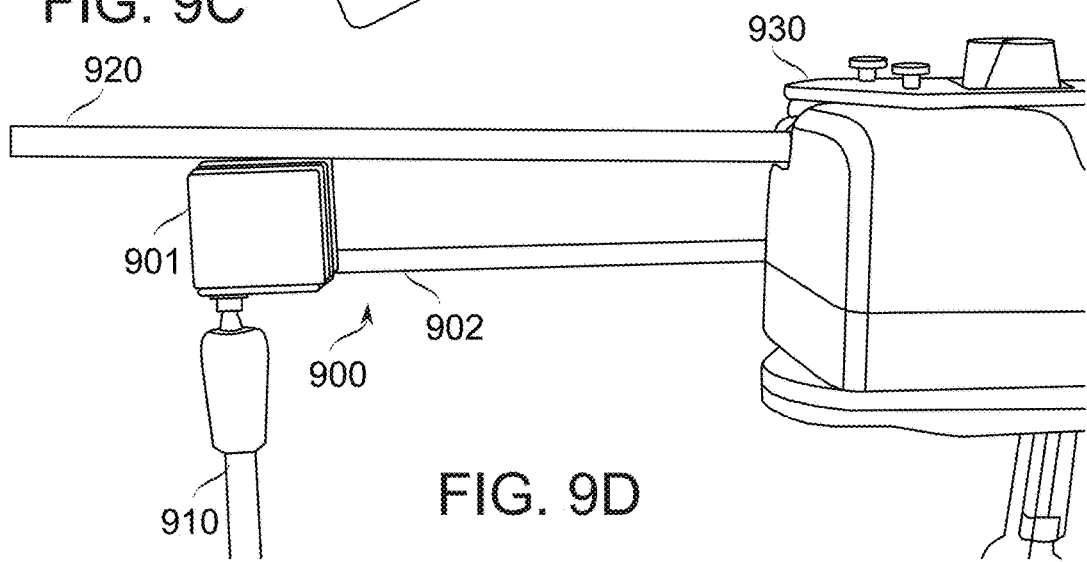
FIG. 9D

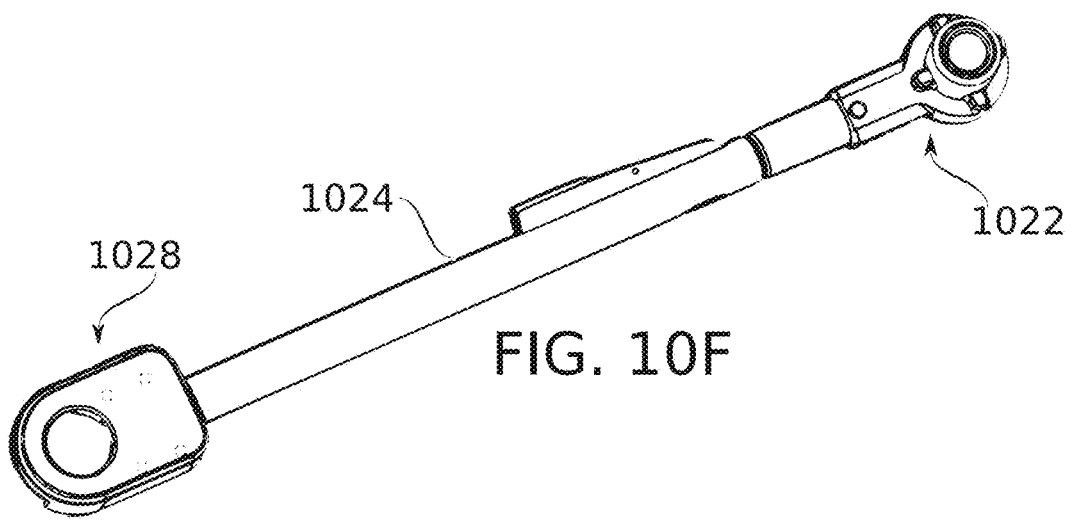
FIG. 10F
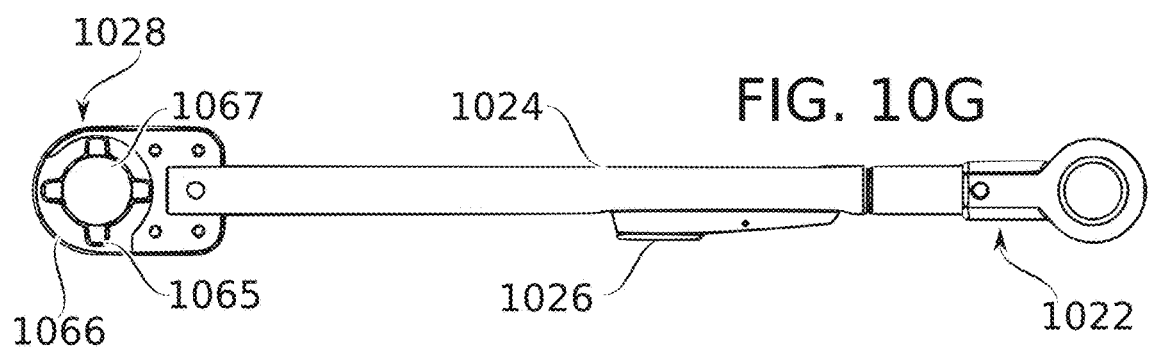
FIG. 10G
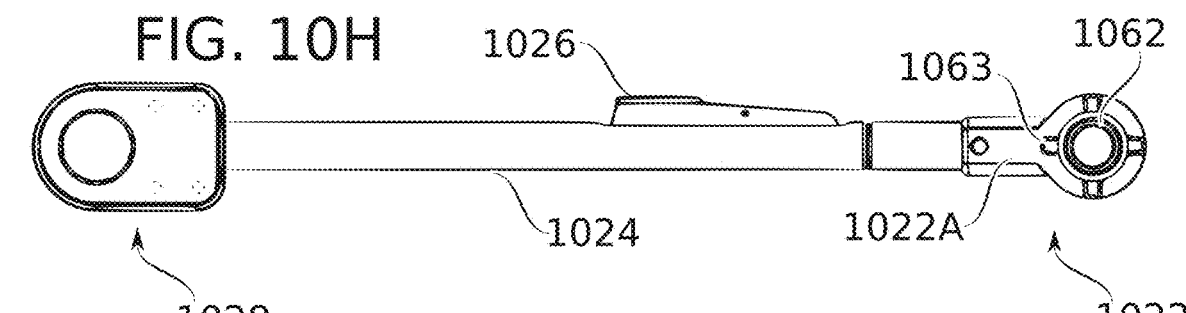
FIG. 10H
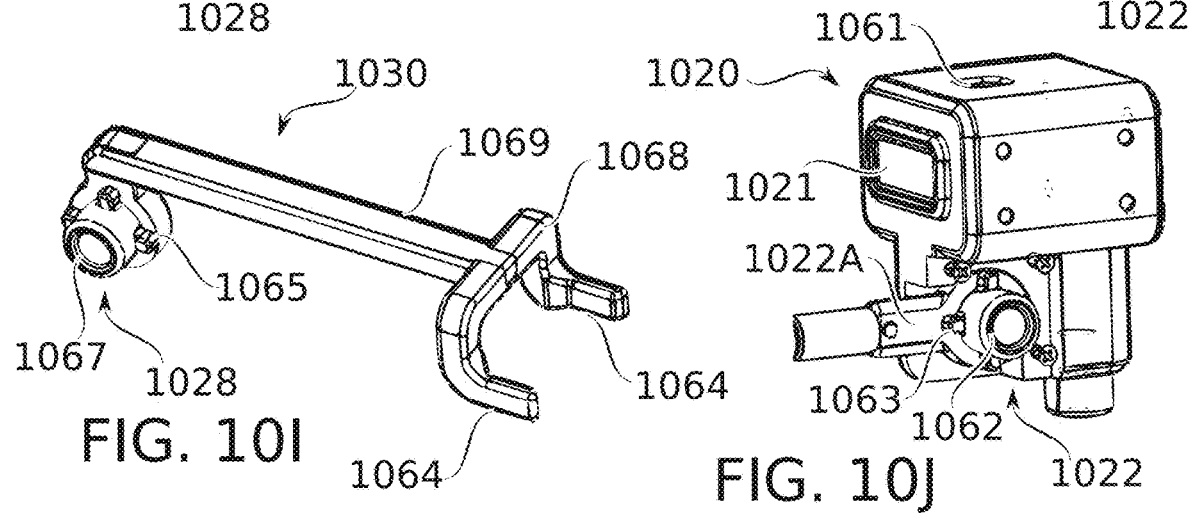
FIG. 10I
FIG. 10J

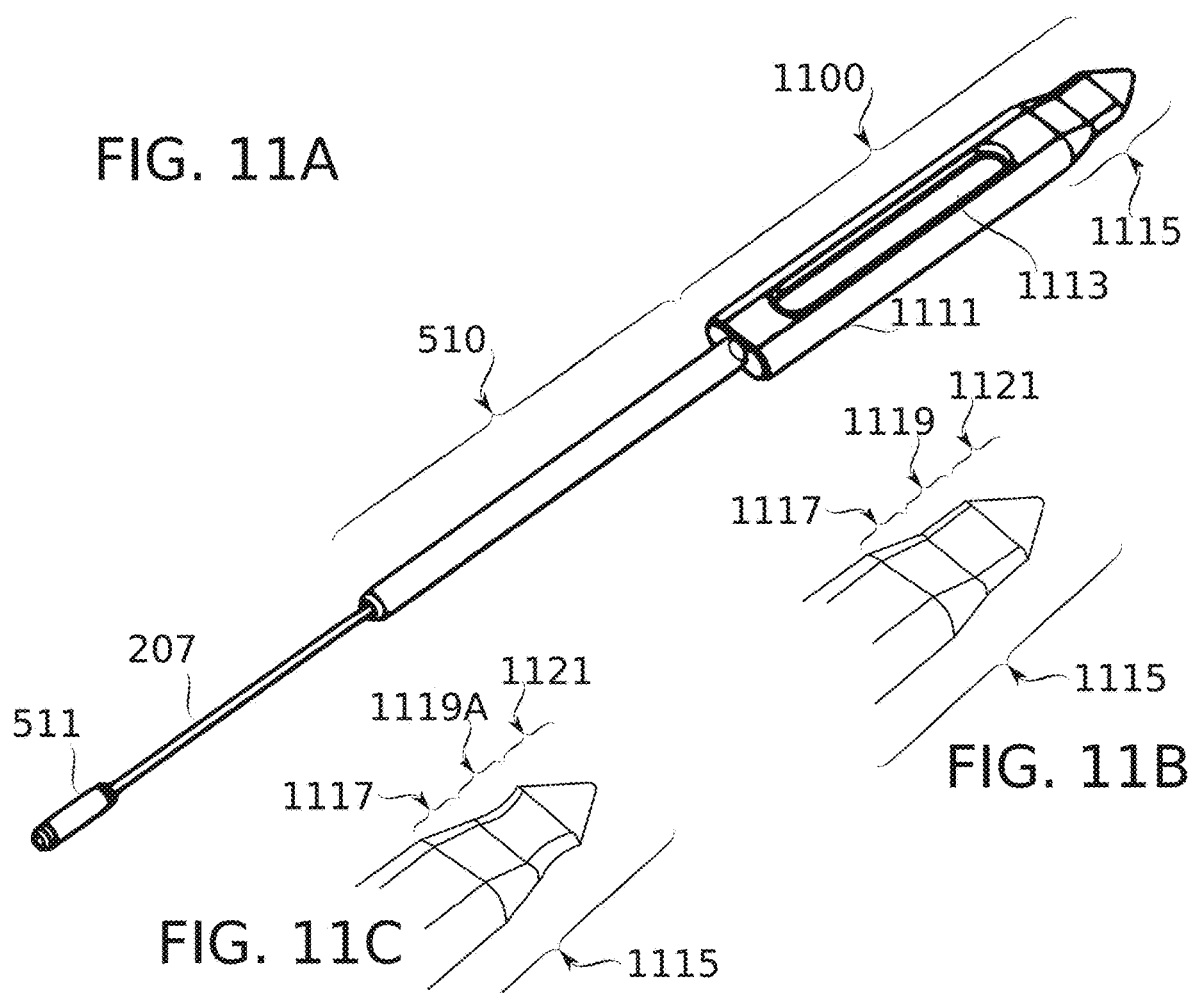
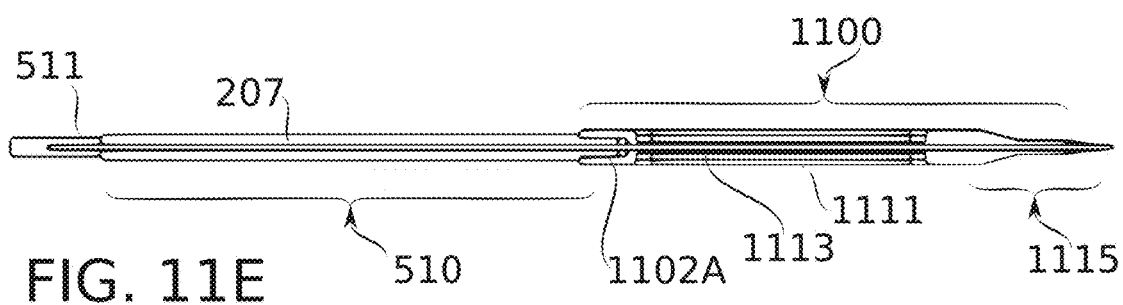

TOOLS AND METHODS FOR VAGINAL ACCESS

RELATED APPLICATIONS

This application claims the benefit of priority of U.S. Provisional Patent Application No. 62/549,097 filed on Aug. 23, 2017; U.S. Provisional Patent Application No. 62/549,078 filed on Aug. 23, 2017; U.S. Provisional Patent Application No. 62/558,460 filed on Sep. 14, 2017; and U.S. Provisional Patent Application No. 62/558,469 filed on Sep. 14, 2017; the contents of which are incorporated by reference as if fully set forth herein in their entirety.

This application is also a part of a set of filings which are co-filed, co-pending and co-assigned:

U.S. patent application Ser. No. 16/109,891 filed on Aug. 23, 2018 entitled "TOOLS AND METHODS FOR VAGINAL ACCESS";

PCT Patent Application No. PCT/IL2018/050934 Having International Filing Date of Aug. 23, 2018 entitled "TOOLS AND METHODS FOR VAGINAL ACCESS";

Canadian Patent Application No. 3,015,084 filed on Aug. 23, 2018 entitled "TOOLS AND METHODS FOR VAGINAL ACCESS");

U.S. patent application Ser. No. 16/109,893 filed on Aug. 23, 2018 entitled "TOOLS AND METHODS FOR VAGINAL ACCESS";

Canadian Patent Application No. 3,015,089 filed on Aug. 23, 2018 entitled "TOOLS AND METHODS FOR VAGINAL ACCESS";

U.S. patent application Ser. No. 16/109,880 filed on Aug. 23, 2018 entitled "TOOLS AND METHODS FOR VAGINAL ACCESS"); and U.S. patent application Ser. No. 14/109,879 filed on Aug. 23, 2018 entitled "TOOLS AND METHODS FOR VAGINAL ACCESS";

the disclosures of which are all incorporated herein by reference.

FIELD AND BACKGROUND OF THE INVENTION

The present invention, in some embodiments thereof, relates to the field of intraperitoneal surgery and more particularly, to devices and methods for laparoscopic access to the intraperitoneal space.

Culdoscopy is an endoscopic procedure performed to examine the rectouterine pouch and pelvic viscera by the introduction of a culdoscope through the posterior vaginal wall. The culdoscope may be a modified laparoscope. A trocar is first inserted through the vagina into the posterior cul-de-sac, the space behind the cervix, allowing then the entry of the culdoscope. Due to the position of the patient, intestines fall away from the pelvic organs which can then be inspected. Conditions diagnosable by culdoscopy include tubal adhesions (causing sterility), ectopic pregnancy, and salpingitis. Culdoscopy allows the performance of minor procedures such as tubal sterilization.

SUMMARY OF THE INVENTION

There is provided, in accordance with some embodiments of the present invention. a stepped dilator for use with a trocar kit to provide intraperitoneal access via a body recess, comprising: a dilator body having a longitudinal axis in proximal to distal direction; a first tapered region of the dilator body tapering narrower toward a distal end of the dilator body; a second tapered region of the dilator body tapering narrower in a distal direction, located proximally to the first tapered region, and separated from the first tapered region by an isolating region.

In some embodiments, the isolating region comprises a region of constant cross-section perpendicular to the longitudinal axis extending between the first tapered region and the second tapered region.

In some embodiments, the isolating region comprises a region with no cross-section perpendicular to the longitudinal axis larger in any direction than the largest cross-section perpendicular to the longitudinal axis of the first tapered region.

In some embodiments, the isolating region is at least 3 mm long.

In some embodiments, the isolating region is no more than 20 mm long.

In some embodiments, the isolating region is between 5-15 mm long.

In some embodiments, a whole tapering extent of at least one of the first tapered region and the second tapered region tapers between its smallest cross-sectional area and its largest cross-sectional area perpendicular to the longitudinal axis over a longitudinal distance of 15 mm or less.

In some embodiments, through the tapering extent of at least one of the first tapered region and the second tapered region, a diameter of the stepped dilator perpendicular to the longitudinal axis increases by at least 7.5 mm.

In some embodiments, a cross-section with the largest cross-sectional area of the first tapered region perpendicular to the longitudinal axis has at least one axis of about 10 mm or longer.

In some embodiments, a distal tip of the first tapered region comprises a front surface aperture of 4 mm2 or less, and expands in a distal direction from the front surface aperture through a radius of curvature of at least 2.5 mm.

In some embodiments, the front surface aperture is an aperture of an inner lumen sized to allow partial advancement of a trocar needle having a diameter less than or equal to about 2 mm in a longitudinal direction through the aperture.

In some embodiments, the cross-section of the first tapered region having the largest cross-sectional area perpendicular to the longitudinal axis has at least one axis of about 7.5 mm or less.

There is provided, in accordance with some embodiments of the present invention: a kit comprising the stepped dilator described above, along with a handle and a trocar needle; wherein the stepped dilator and handle together define a lumen sized to accept passage the trocar needle from a proximal end of the handle to a distal tip of the stepped dilator.

In some embodiments, the trocar needle is provided with a handle extending at least 5 cm past a proximal end of the handle when a distal tip of the trocar needle is advanced 5 mm past the distal tip of the stepped dilator.

In some embodiments, the trocar needle is provided with a dull-tipped, inner, spring-loaded stylet to act as a Veress needle having an extended position and a collapsed position; wherein the stylet comprises a blunt end extending past a sharp tip of the trocar needle in the extended position and preventing the sharp tip from injuring tissue; and wherein the stylet moves to the collapsed position upon sufficient longitudinal force being exerted so that it no longer extends pas the sharp tip, allowing the sharp tip can operate to penetrate tissue.

In some embodiments, provided with a stopper device is configured to resist advancing the distal tip of the trocar needle more than 5 mm beyond the distal tip of the stepped dilator.

In some embodiments, a cross-section with the largest cross-sectional area of the second tapered region perpendicular to the longitudinal axis has at least one axis of about 21 mm or longer.

There is provided, in accordance with some embodiments of the present invention. a cannula to provide intraperitoneal access across a wall of a body recess, wherein a cross-section of an inner lumen of the cannula transverse to a longitudinal axis of the cannula has a long and a short axis; and wherein the long axis is at least twice as long as the short axis.

In some embodiments, the short cross-section axis is between 5 mm and 10 mm.

In some embodiments, the long cross-section axis is between 10 mm and 30 mm.

In some embodiments, a lumenal wall defining the transverse cross-section of the cannula comprises straight sections on opposite sides of the transverse cross-section.

In some embodiments, the straight sections are interconnected through curved sections.

In some embodiments, the cannula is at least 5 cm long.

In some embodiments, an edge defining an aperture at a distal end of the cannula comprises a first edge portion extending along one side of the aperture, and a second edge portion extending along another side of the aperture, wherein the first edge portion extends along a side more distal along the longitudinal axis than the second edge portion.

In some embodiments, the first and second edge portions extend along opposite sides of the aperture.

In some embodiments, the first edge portion and the second edge portion extend along the long cross-section axis.

In some embodiments, the cannula comprises a handle extending at least 10 cm from a proximal end of the cannula.

There is provided, in accordance with some embodiments of the present invention. a cannula for use with a trocar to provide intraperitoneal access via a body recess, wherein an edge defining an aperture at a distal end of the cannula comprises a first edge portion extending along one side of the aperture, and a second edge portion extending along another side of the aperture, wherein the first edge portion extends along a side more distal along the longitudinal axis than the second edge portion.

In some embodiments, the first edge portion is positioned at least 5 mm more distally than the second edge portion.

In some embodiments, the first edge portion and the second edge portion each comprise respective a straight portion.

There is provided, in accordance with some embodiments of the present invention. a method of using a cannula to provide intraperitoneal access to a body cavity via a body recess, comprising: inserting a distal end of the cannula into a dilated aperture of a rectouterine pouch via transvaginal access; wherein an edge defining an aperture at the distal end of the cannula comprises a first edge portion extending along one side of the aperture, and a second edge portion extending along an opposite side of the aperture, and the first edge portion is positioned more distally along the cannula and from the dilated aperture than the second edge portion; and wherein the cannula is inserted so that the aperture at the distal end of the cannula is oriented to open toward the side of the second edge portion and facing toward a rectum adjacent to the rectouterine pouch.

In some embodiments, the method comprises inserting a flexible robotic arm through the cannula and into the rectouterine pouch, so that it exits the aperture in a direction oriented away from the rectum.

In some embodiments, the inserting a distal end of the cannula into the rectouterine pouch comprises sliding the cannula over an outer dilator; the outer dilator has a tapered distal insertion end sized and shaped to fittingly slide over an inner dilator having a tapered distal insertion end with a rounded tip; the cannula slides fittingly over the outer dilator; and at least the outer dilator is inserted into the rectouterine pouch via transvaginal access.

In some embodiments, the method comprises sliding the cannula over the outer dilator while the inner dilator remains within the outer dilator.

In some embodiments, the inserting a distal end of the cannula into the rectouterine pouch comprises sliding the cannula over a stepped dilator; the stepped dilator has a tapered distal insertion end with a rounded tip, a second tapered region, and an isolating region between the second tapered region and the tapered distal insertion end; the cannula slides fittingly over the stepped dilator; and the dilator is inserted into the rectouterine pouch via transvaginal access.

In some embodiments, the rounded tip has a hole sized to pass a trocar needle having a diameter less than or equal to about 2 mm.

There is provided, in accordance with some embodiments of the present invention. a kit for providing intraperitoneal access via a body recess, comprising: a cannula, wherein a transverse cross-section of an inner lumen of the cannula transverse to a longitudinal axis of the cannula has a long axis long enough to allow simultaneous insertion of at least two cylindrical members, each at least 8 mm in diameter; a stepped dilator having a dilator body with: a first tapered region of the dilator body tapering narrower toward a distal end of the dilator body, and a second tapered region of the dilator body tapering narrower in a distal direction, located proximally to the first tapered region, and separated from the first tapered region by an isolating region; and a trocar needle provided with a handle region extending past a proximal end of the inner dilator when a distal tip of the trocar needle is advanced to the distal tip of the inner dilator.

In some embodiments, the long axis of the cannula inner lumen transverse cross-section is at least 21 mm.

In some embodiments, the cannula has a short cross-sectional axis; and wherein the long cross-sectional axis is at least twice as long as the short cross-sectional axis.

In some embodiments, the kit comprises an arm sheath for a plurality of robotic arms, sized to fit within the cannula, having a minimum diameter of about 10 mm, and a maximum diameter of at least twice the minimum diameter.

There is provided, in accordance with some embodiments of the present invention. a method of gaining intraperitoneal access via a body recess, comprising: inserting a first stage of a stepped dilator into a rectouterine pouch to widen an aperture in a wall of the rectouterine pouch; and inserting a second stage of the stepped dilator into the rectouterine pouch to widen the aperture; wherein the first and second stages of the stepped dilator each comprise a region which tapers narrower in a distal direction, and wherein the first and second stages of the dilator are separated by an isolating region at least 3 mm long.

In some embodiments, the method is preceded by: inserting the stepped dilator transvaginally to the wall of the rectouterine pouch; and advancing a trocar needle from within the stepped dilator to produce the aperture in the wall of the rectouterine pouch.

In some embodiments, an inner lumen of the cannula has at least one cross-sectional axis of at least 20 mm.

In some embodiments, the inner lumen of the cannula has at least one cross-sectional axis of less than about 12 mm.

There is provided, in accordance with some embodiments of the present invention. a method of gaining intraperitoneal access via a body recess, comprising: inserting a camera to an intraperitoneal space with a wall of a rectouterine pouch in a field of view of the camera; illuminating the wall of the rectouterine pouch using an intraperitoneally positioned illumination device; selecting a position for an aperture in the wall of the rectouterine pouch, based on light from the illumination device visible from outside the rectouterine pouch; advancing a trocar needle from outside the rectouterine pouch to press against the selected position in the wall of the rectouterine pouch; verifying the position of the trocar needle, based on one or more images from the camera within the intraperitoneal space; and piercing the rectouterine pouch to from the aperture, using the trocar needle.

There is provided, in accordance with some embodiments of the present invention. a kit for setting a position of a robotic arm system along a longitudinal axis of a cannula inserted to a body orifice, wherein the robotic arm system comprises a motor unit and at least one robotic arm extending, when positioned, distally from the motor unit along the longitudinal axis, the kit comprising: the cannula, including a cannula body configured for insertion to the body orifice; a mounting block, configured for attachment to the cannula; and an assembly attached to the mounting block and comprising a spacing arm and an aligning arm, and movable between a stowed position and a deployed position; wherein the deployed position of the assembly places elements of the aligning arm where they indicate a predetermined position along the longitudinal axis.

In some embodiments, the mounting block attaches to the cannula by connecting to an access device having a lumen sized to fittingly accept the cannula therewithin.

In some embodiments, the spacing arm and the aligning arm deploy by hinging around a plurality of stopped hinges, each stopped hinge defining at least a stopped deployed position, and a stopped stowed position.

In some embodiments, the kit further comprises: the motor unit and the at least one robotic arm extending distally from the motor unit to a predetermined distance from a stopper-receiving portion of the motor unit; wherein a distal end of the at least one robotic arm aligns with a distal end of the cannula when the at least one robotic arm is inserted to the cannula, and a stopper portion of the aligning arm contacts a stopper-receiving portion of the motor unit to prevent longitudinal advance of the motor unit.

In some embodiments, the kit comprises an arm sheath with a lumen sized to accept the at least one robotic arm, and an outer surface sized to fit within the cannula.

There is provided, in accordance with some embodiments of the present disclosure, an inner dilator for use with a trocar kit to provide intraperitoneal access via a body recess, having a distal insertion end tapered over a longitudinal distance of 15 mm or less between a distal tip and a fully dilating cross-section of the inner dilator, wherein: the fully dilating cross-section of the inner dilator has at least one axis of about 10 mm or longer; the distal tip of the insertion end comprises a front surface aperture of 4 $mm^2$ or less, and the distal tip of the insertion end expands in a direction along the taper from the front surface aperture through a radius of curvature of at least 2.5 mm; and the front surface aperture is an aperture of an inner lumen sized to allow partial advancement of a trocar needle having a diameter less than or equal to about 2 mm in a longitudinal direction through the aperture.

In some embodiments, the fully dilating cross-section of the inner dilator has at least one axis of about 7.5 mm or less.

There is provided, in accordance with some embodiments of the present disclosure, a kit comprising the inner dilator described above, along with the trocar needle, wherein the inner dilator is at least 17 cm long, and the trocar needle is provided with a handle extending at least 5 cm past a proximal end of the inner dilator when a distal tip of the trocar needle is advanced 5 mm past the distal tip of the inner dilator.

In some embodiments, the trocar needle is provided with a dull-tipped, inner, spring-loaded stylet to act as a Veress needle, wherein the stylet, in its extended position prevents a sharp tip of the needle from injuring tissue, but collapses upon sufficient longitudinal force being exerted so that the sharp tip can operate to penetrate tissue.

In some embodiments, provided with a stopper device is configured to resist advancing the distal tip of the trocar needle more than 5 mm beyond the distal tip of the inner dilator.

There is provided, in accordance with some embodiments of the present disclosure, a kit comprising the inner dilator described above, along with an outer dilator, wherein the outer dilator has a distal insertion end tapered over a longitudinal distance of 15 mm or less between a distal opening and a fully dilating cross-section of the outer dilator, wherein the fully dilating cross-section of the inner dilator has at least one axis of about 21 mm or longer.

In some embodiments, the distal opening has an inner lumen sized to fittingly enclose the fully dilating cross-section of the inner dilator.

In some embodiments, the kit is provided with a stopper configured to resist advancing the distal tip of the outer dilator more than 15 mm beyond the distal tip of the inner dilator.

There is provided, in accordance with some embodiments of the present disclosure, a trocar kit for providing intraperitoneal access via a body recess, comprising: a cannula, wherein a transverse cross-section of an inner lumen of the cannula transverse to a longitudinal axis of the cannula has a long axis long enough to allow simultaneous insertion of at least two cylindrical members, each at least 8 mm in diameter; an inner dilator at least long enough to leave an external handling region of about 10 cm while inserted fully into a body aperture 7 cm long, and having a distal insertion end tapered over a longitudinal distance short enough to reach a complete first-stage dilation within 15 mm or less of movement between a distal tip of 4 $mm^2$ area or less and a fully dilating cross-section of the inner dilator, wherein the fully dilating cross-section of the inner dilator has at least one axis about half as long as the long axis of the cannula cross-section; a trocar needle provided with a handle region extending past a proximal end of the inner dilator when a distal tip of the trocar needle is advanced to the distal tip of the inner dilator; and an outer dilator, wherein the outer dilator has a distal insertion end tapered over a longitudinal distance of 15 mm or less between a distal opening sized to fittingly surround the fully dilating cross-section of the inner dilator, and a fully dilating cross-section of the outer dilator, wherein the fully dilating cross-section of the outer dilator is sized to be fittingly surrounded by the inner lumen of the cannula.

In some embodiments, the long cross-sectional axis of the cannula inner lumen is at least 21 mm.

In some embodiments, the cannula has a short cross-sectional axis; and wherein the long cross-sectional axis is at least twice as long as the short cross-sectional axis.

There is provided, in accordance with some embodiments of the present disclosure, a trocar kit for providing intraperitoneal access via a body recess, comprising: an inner dilator, an outer dilator, and a cannula; wherein: the outer dilator is sized and shaped to fittingly insert over the inner dilator; the cannula is sized and shaped to fittingly insert over the outer dilator; the inner dilator is provided with a rounded distal tip having a hole sized for the longitudinal pass of a trocar needle portion having a diameter less than or equal to about 2 mm; and an inner lumen of the cannula has at least one cross-sectional axis of at least 20 mm; and wherein the inner lumen of the cannula has at least one cross-sectional axis of less than about 12 mm.

In some embodiments, the inner dilator and the outer dilator are each tapered from a respective narrower distal insertion end to a respective full-size cross-section within 15 mm along a longitudinal axis.

There is provided, in accordance with some embodiments of the present disclosure, a method of gaining intraperitoneal access via a body recess, comprising: inserting an inner dilator transvaginally to a wall of a rectouterine pouch; advancing a trocar needle from within the inner dilator to produce an aperture in the wall of the rectouterine pouch; inserting the inner dilator no more than 15 mm into the rectouterine pouch to widen the aperture; inserting an outer dilator no more than 15 mm into the rectouterine pouch by sliding the outer dilator over the inner dilator and across the aperture while the aperture is held open by the inner dilator; and inserting a distal end of a cannula into the rectouterine pouch by sliding the cannula over the outer dilator and across the aperture while the aperture is held open by the outer dilator; wherein an inner lumen of the cannula has at least one cross-sectional axis of at least 20 mm.

In some embodiments, the inner lumen of the cannula has at least one cross-sectional axis of less than about 12 mm.

There is provided, in accordance with some embodiments of the present disclosure, a method of gaining intraperitoneal access via a body recess, comprising: inserting a camera to an intraperitoneal space with a wall of a rectouterine pouch in a field of view of the camera; illuminating the wall of the rectouterine pouch using an intraperitoneally positioned illumination device; selecting a position for an aperture in the wall of the rectouterine pouch, based on light from the illumination device visible from outside the rectouterine pouch; advancing a trocar needle from outside the rectouterine pouch to press against the selected position in the wall of the rectouterine pouch; verifying the position of the trocar needle, based on one or more images from the camera within the intraperitoneal space; and piercing the rectouterine pouch to from the aperture, using the trocar needle.

There is provided, in accordance with some embodiments of the present disclosure, a kit for setting a longitudinal position of a robotic arm system along a longitudinal axis of a cannula inserted to a body orifice, wherein the robotic arm system comprises a motor unit and at least one robotic arm extending distally from the motor unit along the longitudinal axis, the kit comprising: a cannula, including a cannula body configured for insertion to the body orifice and a cannula handle extending proximally along a longitudinal axis of the cannula; a mounting block, including a block body and a clamp configured to clamp the cannula handle at a selected longitudinal position relative to the block body; and a motor unit stopper, including a longitudinally extended member attached to the block body, and movable between: a first position extending a predetermined length from the block body to a proximal end of the motor unit stopper, and a second position; wherein the proximal end of the motor stopper unit in the first position is positioned to contact and prevent longitudinal advance of the motor unit upon insertion of the at least one robotic arm to the cannula, thereby defining a predetermined longitudinal position of the robotic arm system relative to the cannula; and wherein the second position of the motor unit stopper removes the motor unit stopper proximal end from a position preventing the longitudinal advance of the motor unit from the predetermined longitudinal position.

In some embodiments, the motor unit stopper is attached to the block body by a hinge, the first position comprises orientation of the motor unit stopper along the longitudinal axis of the cannula, and movement between the first position and the second position comprises rotation of the motor unit stopper on the hinge.

In some embodiments, the motor unit stopper is movable between the first position and the second position without disturbing the position of either the cannula or the motor unit when the at least one robotic arm is inserted to the cannula.

In some embodiments, the kit further comprises: the motor unit and the at least one robotic arm extending distally from the motor unit to a predetermined distance from a stopper-receiving portion of the motor unit; wherein a distal end of the at least one robotic arm aligns with a distal end of the cannula when the at least one robotic arm is inserted to the cannula, and the motor unit stopper contacts the stopper-receiving portion of the motor unit to prevent longitudinal advance of the motor unit.

In some embodiments, the kit comprises a plurality of extenders, each comprising a tube with a lumenal cross-section sized to receive a robotic arm having a cross-sectional axis of at least 7 mm, and a length sized to extend longitudinally from the proximal end of the stopper to a position distal to the longitudinal position of the block body.

In some embodiments, the block body is slotted to receive the plurality of extenders at a position and orientation allowing guidance of robotic arms along the longitudinal axis to an aperture of the cannula body.

There is provided, in accordance with some embodiments of the present disclosure, a kit comprising an inner dilator having a distal tip sized to partially dilate an incision, and an outer dilator sized to slide distally over the inner dilator to further dilate the incision with a distal tip of the outer dilator, wherein: the overall dilation of the inner and outer dilators is at least enough to allow simultaneous insertion of at least two cylindrical members each having a diameter of at least about 8 mm, while a longitudinal distance along each of the inner and outer dilators over which dilation occurs is less than about 20 mm; at least one of the inner dilator and the outer dilator are marked near a proximal end to indicate a relative position at which the two dilators are positioned, including at least a mark indicating alignment of the distal ends of the two dilators, and a mark indicating a longitudinal position difference of one dilator relative to the other of the longitudinal distance over which dilation occurs.

In some embodiments, both the inner and outer dilators are marked with a distance scale indicating distance along each dilator to its distal end.

In some embodiments, the distance scales of the inner and outer dilators are numerically aligned when the distal ends of each are aligned.

In some embodiments, the kit comprises an indicating indexer configured to change the force needed to translate the inner and outer dilators longitudinally over one another, depending on the relative longitudinal positions of the inner and outer dilators.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the present disclosure are described, by way of example only, with reference to the accompanying drawings. With specific reference now to the drawings in detail, it is stressed that the particulars shown are by way of example, and for purposes of illustrative discussion. In this regard, the description taken with the drawings makes apparent to those skilled in the art how embodiments of the present disclosure may be practiced.

In the drawings:

FIGS. 3A-3H schematically represent a method of using trocar components to establish intraperitoneal access through rectouterine pouch wall or another body wall, according to some embodiments of the present disclosure;

FIG. 3I schematically represents the cannula configure of FIG. 3H, along with inserted tools, according to some embodiments of the present disclosure;

FIG. 3J is a schematic flowchart outlining preparation for a laparoscopic procedure using trocar, according to some embodiments of the present disclosure;

FIGS. 9A-9D comprise views representing an instrument holder for cannula and its configuration for use, wherein instrument holder includes a motor unit stopper for use in setting an initial robotic arm position, according to some embodiments of the present disclosure;

FIGS. 10F-10J schematically represent components of collapsing instrument holder, according to some embodiments of the present disclosure;

FIGS. 11A-11E schematically represent a stepped dilator, dilator handle, and trocar needle, according to some embodiments of the present disclosure.

DESCRIPTION OF SPECIFIC EMBODIMENTS OF THE INVENTION

Figure 1:
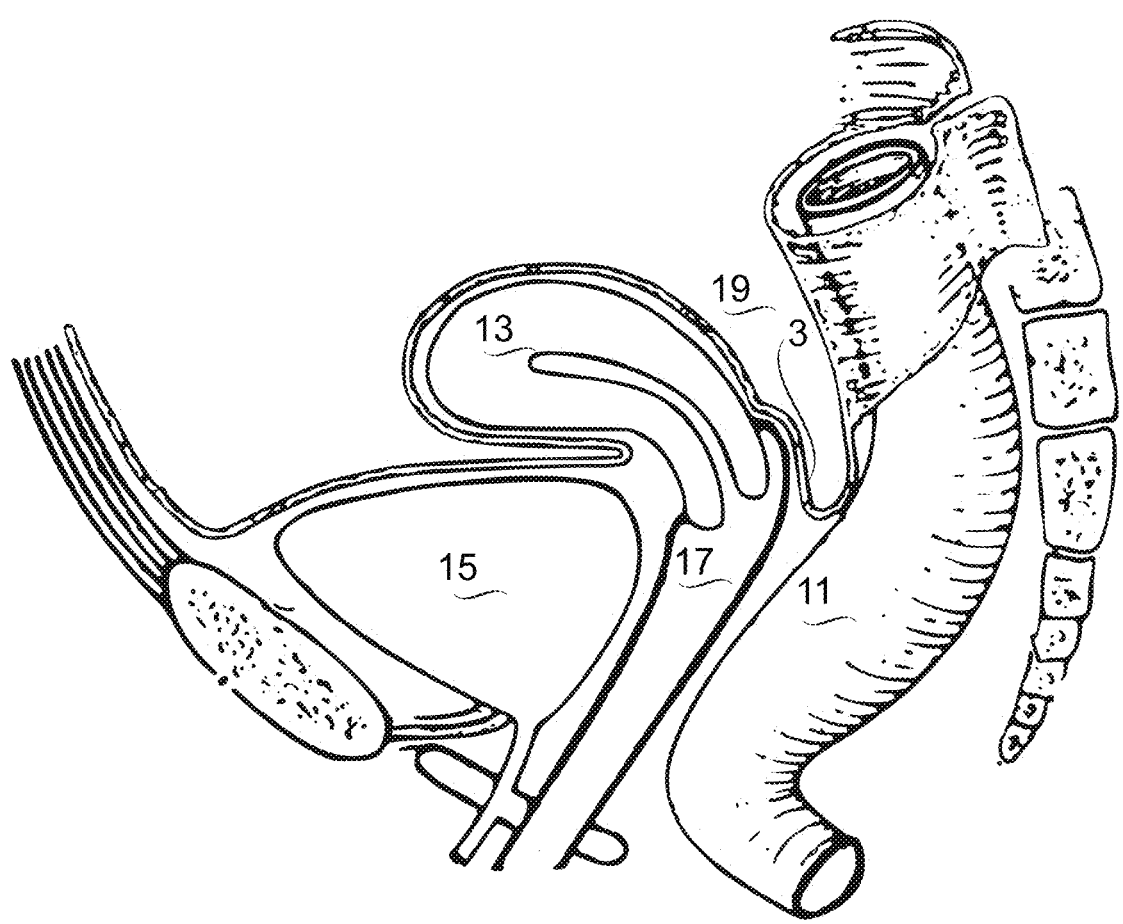
FIG. 1 is a schematic representation of portions of a human female pelvic anatomy, referenced by descriptions herein according to some embodiments of the present disclosure.

The present invention, in some embodiments thereof, relates to the field of intraperitoneal surgery and more particularly, to devices and methods for laparoscopic access to the intraperitoneal space.

Overview

A broad aspect of some embodiments of the present invention relates to trocar components (provided individually and/or in kits) configured to provide access to intraperitoneal space via the rectouterine pouch for surgical tools, optionally including one or more surgical robot members (herein, "robotic arms"). Compared, for example, to umbilicus entry to the intraperitoneal space, rectouterine pouch access to the peritoneal space provides potential advantages for reduced invasiveness, reduced patient trauma, reduced visible scarring, and/or speed of the operation.

An aspect of some embodiments of the present invention relates to a cannula having a lumen with an oblong cross-section, and configured to simultaneously accept two or more substantially cylindrical tools extending side-by-side along the lumen.

In some embodiments, a cannula part is provided which has sufficient longitudinal length to extend between a wall of the rectouterine pouch and a position near to the entrance to the vagina, for example, about 7-15 cm long. Optionally, an intravaginal length of cannulation is selectably extended (e.g., between from 7 up to about 15 cm) by use of the cannula together with an additional part; for example, a trocar part, with which it may be telescopically mated. Alternatively, in some embodiments, a selection of different cannula lengths is provided (e.g., in a length range of from 7 to 15 cm, for example, at least three cannulas in this range; and optionally cannulas of sizes in about 1 cm or 2 cm length increments from each other). This provides a potential advantage for avoiding a possibility of pinching between two telescoping cannula portions.

Optionally, the cannula lumen cross-section is sized to provide simultaneous, side-by-side intraperitoneal access to two substantially cylindrical (e.g., tubular) tools having a diameter of about 8.6 mm. In some embodiments, the substantially cylindrical tools comprise tube-shaped robotic arms. The cannula lumen cross-section, in some embodiments, has a longest axis at least twice as long as a shortest axis. Optionally, the cannula cross-section is sized so that there is also room for a third tool having a cross-section with a maximum axis length of about 6 mm or less. Compared to a circular cross-section sized to pass two or more such cylindrical tools, such an oblong cross-section provides a potential advantage for allowing a smaller overall cannula perimeter, with a correspondingly smaller incision needed to accept the cannula.

In some embodiments, the cannula has a distal aperture which is slanted relative to the longitudinal axis of the cannula so that it opens toward the direction of intraperitoneal space when inserted into the rectouterine pouch. Potentially, this helps to provide space for robotic members and/or other tools to bend to enter the intraperitoneal space.

Optionally, the cannula is constructed from stainless steel or another material which can be sterilized and re-sterilized to surgical use standards. Optionally, the cannula is disposable and provided in a sterilized condition.

An aspect of some embodiments of the present invention relates to geometries of dilators configured to achieve incision dilation while advancing to longitudinal distances kept short and/or controlled to avoid trauma to delicate tissues near the rectouterine pouch; and to methods of dilation adjusted for the geometries of the dilators.

A significant potential complication of opening a rectouterine pouch incision to the intraperitoneal space is damage to the rectum. The damage may be due for example, to over-penetration causing puncture, scraping, and/or crushing during initial puncture and/or dilation of the incision. In some embodiments, a constraint on maximum longitudinal advance is set by the width of the rectouterine pouch, and a need to reduce the potential for accidental damage to nearby internal organs, for example, the rectum.

In some embodiments of the invention, features of a trocar kit and/or its method of use potentially act to reduce a risk of injury due to over-penetration during cannulization. In particular, target insertion depth (e.g., minimum depth at full dilation) is kept low in some embodiments (e.g., dilation of up to about 7.5-15 mm occurs over about 10-20 mm of longitudinal insertion depth, for example, 13 mm, 15 mm, 17 mm, 19 mm, or 20 mm). In some embodiments, dilation occurs over about up to 30 mm, 40 mm, or 50 mm of insertion depth.

Overall insertion depth by a dilator after dilation itself is complete is optionally somewhat larger than this (e.g., up to about 2-5.5 cm). However, application of potentially injurious force is particularly likely during a dilating phase in which the expanding portion of the dilator is being advanced through an incision—since this is the phase of dilator operation during which overcoming resistance by use of additional force is expected and normal.

Optionally, insertion in a dilating phase of operation to an excessive depth is treated as itself having a higher risk of causing injury (e.g., due to the internal proximity of delicate tissues) than the elevation of maximum peak insertion force that may result from the lowered mechanical advantage of a shortened dilation depth.

In some embodiments, dilators are provided as a pair of dilators. In some embodiments, the pair of dilators comprises a first dilator and a second dilator, wherein the first dilator is smaller in cross-section than the second dilator. Optionally, the first dilator is provided as an "inner" dilator relative to the second, larger and "outer" dilator. The inner and outer dilators are configured to slide longitudinally relative to one another.

In some embodiments, a dilator is provided as a single dilator which dilates using a stepwise plurality of staged dilator expansions (e.g., two or three).

In some embodiments, each dilator or dilator step provides expansion from an initial incision width (smallest cross-sectional area of the dilator stage) to a final incision width (largest cross-sectional area of the dilator stage) within about 15 mm of longitudinal advance per stage. Optionally the expansion occurs within another longitudinal distance of advance, for example, a distance from within the range of about 10-20 mm, for example, 13 mm, 15 mm, 17 mm, 19 mm, or 20 mm.

The amount of widening over the travel of the dilator stage is optionally itself in the range of about 7.5-15 mm, for example, about 7.5 mm, 10 mm, 12 mm, 12.5 mm, or 15 mm. This fairly rapid rate of dilation as a function of longitudinal advance accepts loss of mechanical advantage in exchange for a reduced required insertion depth to complete dilation. Total insertion depth during dilation can be about the length of a single step (optionally plus a few millimeters past the expanding part of the dilator, e.g., plus 5-10 millimeters) when a plurality of dilators are used; wherein a subsequent dilator is inserted over the previous dilator. When a single (stepwise expanding) dilator is used, insertion depth during dilation may be the sum of the lengths of the individual dilation stages; plus an optional isolating region between the dilation steps having a length of, for example, about 5-15 mm; and optionally plus a few more millimeters (e.g., 5-10 mm) past the expanding part of the dilator. For example, the total insertion depth may be about 50 mm. In some embodiments, the isolating region is at least 3 mm long. Additionally or alternatively, the isolating region is less than about 20 mm long.

Related to this, the inventors have realized that mechanical properties of the pouch wall tissue related to resisting dilation (e.g., resistance to tearing and/or stretching) are potentially more permissive of a lowered mechanical advantage than the mechanical properties of the walls of other intraperitoneal access positions, for example, the mechanical properties of the skin, fat, and/or muscle layers of the umbilical region. This has allowed use of a dilator design which has reduced mechanical advantage (is blunter), in exchange for such potential advantages as a shorter dilator insertion depth and/or a smaller number of dilation steps.

Dividing the dilation into stages (e.g., by using a plurality of dilators and/or a plurality of isolated dilation steps) potentially gives greater control over dilation by providing a stopping point mid-dilation. This potentially reduces a chance of uncontrolled tearing during dilation, and/or allows inspection of initial dilation to ensure that there is no unexpected damage (e.g., excessive bleeding) which might be aggravated by further dilation.

In some embodiments, the first dilator and/or dilator step has a blunted distal-most portion. The distal-most portion optionally has a port through which a trocar needle can be extended. Optionally, the distal-most portion curves proximally, widening in both width and height through a radius of at least about 2.5 mm, then expanding primarily in width to form a wide oblong cross-section about 15 mm proximal to the distal-most portion (or another distance, for example in the range of about 10-20 mm).

In some embodiments, the second dilator and/or dilator step has a distal-most portion defining a lumen sized to fittingly slide over the first dilator. The outer perimeter of the distal-most cross-section is only slightly larger than the oblong cross-section at the proximal end of the expanding cross-section region of the first dilator. From there, the second dilator's cross-section also expands going proximally for about 15 mm (or another distance, for example in the range of about 10-20 mm). The maximum of the further expansion is by about, for example, about 5 mm, 7.5, mm, 10 mm, or 12.5 mm. Optionally, there is a larger expansion along one axis of the incision cross-section than along another axis; for example, there may be a relative factor of expansion of about 1:1.5, 1:2, or 1:3.

In some embodiments, the cannula is sized to fittingly slide over the second dilator to reach a position with its distal aperture inserted within the rectouterine pouch.

In some embodiments, the trocar needle used with the first dilator is provided together with a holder and/or handle which are sized so that the maximum distal advance of the trocar needle is limited by interference between the handle and/or the holder. In some embodiments, the dilators are provided with a stopper and/or indicating indexer which allow tracking of their relative position, and/or resist, indicate, and/or prevent over-advancement of one dilator relative to the other.

Optionally, the dilator, dilators, handle, holder, and/or trocar needle are constructed from stainless steel or another suitable material which can be sterilized and re-sterilized to surgical use standards (e.g., by autoclaving). Optionally, one or more of these parts is disposable and provided in a sterilized condition.

An aspect of some embodiments of the present invention relates to dilator safety performance maintained and/or enhanced by feedback features and/or methods which help monitor dilator advancement.

In some embodiments, a potential for loss of control of position (e.g., sudden accidental over-advancement as tissue gives way, and/or as the end of the expanding region of the dilator is reached) is reduced by moving each dilator with respect to a fixed (e.g., clamped to the patient table) reference. For example, the first dilator is moved with reference to its initial position and/or an already inserted needle; and/or the second dilator is moved relative to the inserted position of the first dilator. Monitoring of position relative to a fixed reference position potentially encourages a user of the dilators to ease back on force when nearing a dilator's target position.

In some embodiments, a stopper arrangement changes (e.g., increases) a sliding resistance between two components in relative motion as a target dilator advancement limit is approached and/or reached. The change may indicate reaching a target position to a user, and/or mechanically resist advance beyond the target position.

An aspect of some embodiments of the present invention relates to methods of cannulizing a rectouterine pouch wall while monitoring the penetration using information communicated across the rectouterine wall. In some embodiments, initial rectouterine pouch penetration (e.g., using a trocar needle) is visualized from using a camera and/or light source already inserted to the intraperitoneal space from another location, for example, the umbilical. Upon needle contact, a region of indentation may be interiorly observed before actual puncture. Alternatively or additionally, transillumination of the rectouterine pouch wall by an intraperitoneally located light source is observed from outside the pouch in order to help position a needle used for initial penetration. The method has a potential advantage insofar as the rectouterine wall is located both in a difficult region to directly access (due to its position deep within the vagina), and nearby sensitive internal structures which could lead to surgical complications if damaged during cannulization. Dual inside-to-outside and outside-to-inside needle position verification allows seeing from the outside (by the illumination) that the targeted port position (aimed at by a needle which is to create an initial opening) is in a reasonable location relative to internal structures which are to be targeted/avoided, and then confirming that the actual port position which the needle will create really is at the position aimed at.

It is noted that the method described with respect to the rectouterine pouch may be adapted to cannulization of other areas, wherein a first introduction of a camera and light source is from a first port into an intrabody space, and cannulization is to be performed to create another port in a region which perhaps provides some advantage (e.g., better suited to receive a larger incision which is needed for larger tools, and/or provides a preferred direction and/or position of access by the tools), but may also be at greater risk of complication during its creation (e.g., because it is in a region which is more difficult to target externally, and/or because it is associated with certain safety risks if performed incorrectly). More generally, in some embodiments, where a plurality of ports are to be used, second and subsequent ports may be opened under two-sided observation after camera and lighting are established within a first port.

An aspect of some embodiments of the present invention relates to achieving dependable and preferably rapid initial positioning of robotic arms relative to a cannulated surgical access-way. The cannula helps to provide access to a region of surgical activity which is not only internal, but also positioned at the end of a restrictive tunnel. The robotic arms themselves may be articulated along their length in such a way that the result of a commanded motion is different depending on exactly what their starting position is relative to the potential restrictions on motion presented by the cannula and/or the geometry of the internal body space in which they are operated.

Two parameters of particular importance are the distance of longitudinal advance of one or more robotic arms through the lumen of the cannula, and the angle of approach of the one more robotic arms. An incorrect distance of longitudinal advance potentially leads to unexpectedly restricted motion (e.g., because an articulated arm portion has not advanced out of the cannula as much as expected), or even injury (e.g., a collision with body tissue due to over-advancing). An incorrect angle of approach potentially leads to torquing of the robotic arms and/or cannula due to mutual interference as the robotic arms advance. In some more extreme cases, this could lead to difficulty with robotic arm advance, and/or to disturbance of the cannula position. Even if the alignment is correct enough to achieve safe robotic arm introduction to the region of surgical activity, robotic arms may not perform fully as expected, because of lateral interference forces. Such forces are potentially hard to judge by visual inspection to allow correction or compensation.

These concerns potentially applies to one or both of robotic arm movements fully under the direct guidance of a surgeon, and robotic arm movements which are at least partially under automatic control. Moreover, it can be difficult to judge the angle of approach and initial distance of longitudinal advance required for intended device operation, potentially leading to an iterative and/or painstaking setup period before the surgery can begin.

In some embodiments of the present invention, apparatus elements attached to the cannula are deployed to provide indications of where a robotic arm device should be placed. In some embodiments, these elements include spacing devices and/or guides which, once deployed, provide clear indications of whether robotic arm-cannula alignment is correct, and/or help to prevent incorrect alignments.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Dilator and Cannula for Rectouterine Pouch Access

Reference is now made to FIG. 1, which is a schematic representation of portions of a human female pelvic anatomy, referenced by descriptions herein according to some embodiments of the present disclosure.

Referenced in particular by descriptions herein is rectouterine pouch 19, including a portion of rectouterine pouch wall 3 accessible from vagina 17. Also shown in FIG. 1 are bladder 15, uterus 13, and rectum 11. As shown, uterus 13 is in an anteverted position (i.e., tilted forward toward the bladder). In a significant number of patients, uterus 13 may be retroverted (i.e., tilted posteriorly), or in another position. In some embodiments, a retroverted uterus can be manipulated into a position which improves intraperitoneal access through the rectouterine pouch 3; for example, by use of a uterine manipulator.

Figure 2A:
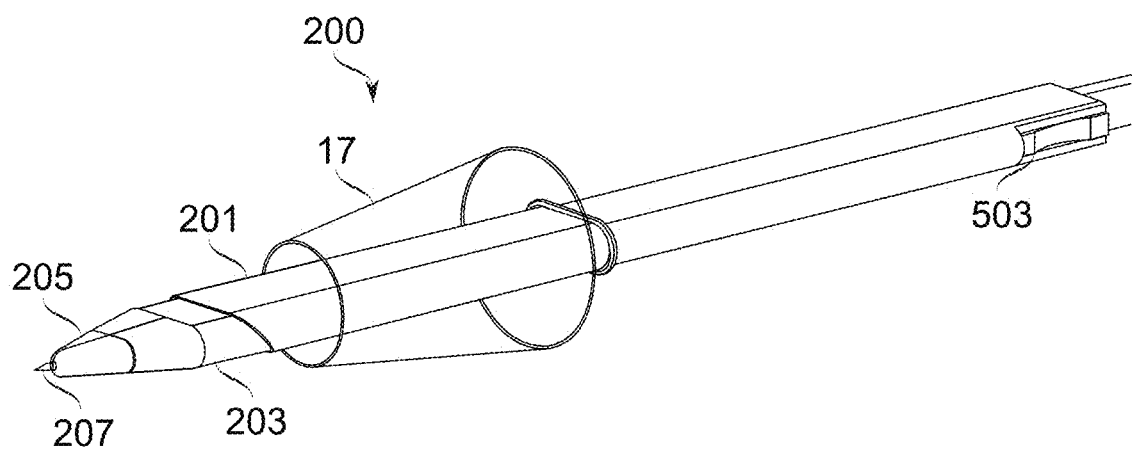
FIG. 2A schematically represents a kit of trocar components, according to some embodiments of the present disclosure.

Reference is now made to FIG. 2A, which schematically represents a kit of trocar components 200, according to some embodiments of the present disclosure.

In some embodiments, the trocar components 200 are sized and shaped to open an intraperitoneal aperture in the rectouterine pouch 19, transvaginally via vagina 17.

In some embodiments, trocar components 200 comprise a trocar needle 207, an inner dilator 205, an outer dilator 203, and/or a cannula 201, 1010. The components are optionally sized and shaped to be nested one within the next in the order listed. Optionally, a distance of longitudinal advancement of trocar components 200 along one another is indicated and/or limited by use of a stopper and/or indicating indexer, for example, leaf spring device 503 or another device, for example as described in relation to FIGS. 5A-5C herein.

Figure 2B:
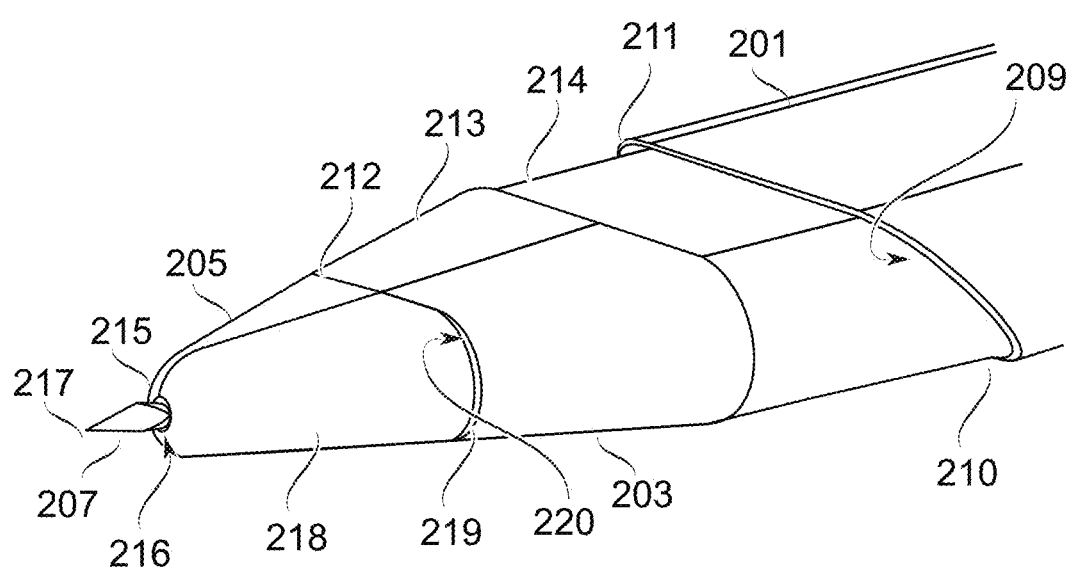
FIG. 2B schematically represents distal portions of components in the kit of trocar components, according to some embodiments of the present disclosure.

Reference is now made to FIG. 2B, which schematically represents distal portions of components in the kit of trocar components 200, according to some embodiments of the present disclosure. Reference is also made to FIGS. 3A-3H, which schematically represent a method of using trocar components 200 to establish intraperitoneal access through rectouterine pouch wall 3 or another body wall, according to some embodiments of the present disclosure.

While FIGS. 3A-3H illustrate a two-dilator expansion procedure, it is to be understood that more dilators (e.g., three, four, five, or more) are optionally used. Using more dilators is optionally coupled to steeper-sloped dilator tip designs (i.e., less expansion per mm of advance), which can help to reduce resistance to insertion. Optionally, only one dilator is used (for example as described in relation to FIGS. 6A-6E herein). The inventors have found that two dilators, each expanding along a longitudinal distance of about 15 mm, are apparently enough to reach a fully dilated size of about 30 mm×10 mm, without undue use of insertion force and/or elevated risk of patient injury. In particular, 15 mm appears to be a safe distance of direct penetration through a vaginal wall 3 into rectouterine pouch 19, which does not carry a significant risk of accidental injury to the adjacent rectum 19.

In FIG. 3A, a distal end of inner dilator 205 is shown advanced to wall 3 of rectouterine pouch 19, e.g., with blunt tip 215 positioned in contact with wall 3. The advance is made transvaginally, in some embodiments. Vagina 17 is not shown in the sequence of FIGS. 3A-3H, but may be understood to surround distal portions of the trocar components near the rectouterine pouch wall 3.

In FIG. 3B, a sharp tip 217 of trocar needle 207 is advanced out of a distal port 216 of inner dilator 205 sufficiently to puncture wall 3 and enter rectouterine pouch 19.

Optionally, trocar needle 207 is no more than 2 mm in diameter (distal port 216 is sized large enough to pass trocar needle 207; for example, distal port 216 may be about 2.1 mm in diameter to pass a trocar needle 207 having a 2 mm diameter). Potentially, this limitation on diameter helps to reduce a risk of serious complications developing in the case of accidental penetration into rectum 11. Optionally, trocar needle 207 comprises a Veress needle having a blunt, spring-loaded center stylet which in its extended position prevents the sharp tip of the needle from injuring tissue, but collapses upon sufficient longitudinal force being exerted so that the sharp tip can operate to penetrate tissue. Such a needle potentially serves to prevent unintended injury (e.g., penetration to the rectum 11) during penetration of the wall 3 of the rectouterine pouch 19.

In some embodiments, trocar needle 207 is restrained by a stopper device from protruding more than a few millimeters (e.g., no more than about 3 mm, 5 mm, 8 mm, or 10 mm) from the distal tip of inner dilator 205 by a stopper and/or indicating indexer. Potentially, the restriction on protrusion reduces opportunity for the needle cause injury by over-penetrating the outer tissue wall to be dilated and injuring an internal tissue surface. A penetration distance chosen, e.g., 5 mm, may be enough to stretch and puncture with the trocar needle 207 an outer tissue wall having tissue pressed against the inner dilator 205, while being short enough that puncture of any deeper tissue layer beyond the outer tissue wall is prevented. A method of positioning trocar needle 207 for penetration is described, for example, in relation to FIG. 4, herein.

In the position of FIG. 3C, inner dilator 205 is advanced through the hole opened by trocar needle 207, up to about the wide cross-section 219 of the distal region of inner dilator 205. During the advance, blunt tip 215 of inner dilator 205 is first pushed into the hole in wall 3 made by needle 207. Further advance of dilator 205 widens the hole in wall 3 according to the expansion of the tip through tapering region 218 of dilator 205 between blunt tip 215 and wide cross-section 219. In some embodiments, a first (distal) dilating stage of stepped dilator 1100 (that is, a portion of dilator 1100 comprising distal tapering region 1121) is used for these operations.

In some embodiments, the overall distance between wide cross-section 219 and the distal-most profile of blunt tip 215 (at distal port 216) is about 15 mm. Potentially, this distance is short enough to prevent injury to the wall of the rectouterine pouch 19 opposite to the wall 3 which inner dilator 205 penetrates (e.g., short enough to prevent injury to the rectum). However, providing some distance of expansion allows the widening slope of the dilator tip to provide mechanical advantage during insertion, so that tissue at the puncture is widened gradually. In some embodiments, another dilator tip length is used, for example about 10 mm, 12 mm, 14 mm, 16 mm, or 18 mm.

In some embodiments, blunt tip 215 rounds back from a substantially flat distal-most profile with a radius of curvature of about 2.5 mm. While a blunt profile potentially results in initially higher resistance to the advance of inner dilator 205, the blunt tip profile has the potential advantage of reducing a likelihood of injury to the wall of the rectouterine pouch 19 opposite to the wall 3 which inner dilator 205 penetrates (e.g., short enough to prevent injury to the rectum).

Optionally, cross-section 219 is about 20 mm across its longest axis, and about 10 mm across its shortest axis. Optionally, the largest axis of the inner dilator 205 at cross-section 219 is about, for example, 15 mm, 16 mm, 17 mm, 18 mm, 19 mm, or 20 mm. Optionally, the shortest axis of cross-section 219 is, for example, about 5 mm, 7 mm, 8 mm, 10 mm, 11 mm or 13 mm. Optionally, the ratio between the longest axis and the shortest axis is, for example, about 1.5, 2 2.5, 3, or 3.5. In some embodiments, the expansion of one or both of the longest axis and the shortest axis of cross-section 219 uses the whole available length of the dilator tip. In some embodiments, proximal-going expansion across the shortest cross-sectional axis occurs over a distance of, for example, about 2.5 mm, 3 mm, or 4 mm of longitudinal travel, then levels out. Optionally, proximal-going expansion across the longest cross-sectional axis occurs over a distance of, for example, about 8 mm, 10 mm, 12 mm, 13 mm, 15 mm, or 18 mm.

Optionally, the expansion of the longest cross-sectional axis through tapering region 218 is substantially linear as a function of longitudinal distance for a portion of inner dilator 205 leading up to wide cross-section 219. Optionally the expansion is non-linear, e.g., curved to expand faster and/or slower as the overall perimeter of the entry hole into wall 3 grows larger. For example, a relatively blunt tip potentially takes advantage of tissue compliance due to elasticity around an initially small entrance incision, while a more gradual cross-section expansion is used where non-elastic expansion (e.g., by tearing) dominates.

Optionally, there is a gradual increase in expansion rate (slope) moving still further proximally. Potentially, this allows percentage stretch of a hole perimeter as a function of longitudinal advance is maintained at a lower initial value than would be produced by a more linear expansion over the same distance. This may reduce resistance to insertion, potentially reducing a risk of trauma. Optionally, either linear or non-linear expansion is used through tapering region 213 of outer dilator 203.

In some embodiments, needle 207 is retracted before and/or as inner dilator 205 is advanced, potentially reducing a risk of injury to the opposite wall. In some embodiments, the distance of advance of inner dilator 205 is controlled by recording the position of inner dilator 205 upon needle penetration, and comparing that position to more advanced positions. Optionally, a stopper is positioned after initial penetration by needle 207 and locked into place relative to the patient (e.g., locked to the table by a positioning arm) so that no more than a predetermined total advance distance (e.g., 15 mm) is allowed.

In FIG. 3D, outer dilator 203 is shown longitudinally advanced over inner dilator 205 until it reaches wall 3 of rectouterine pouch 19 (e.g., so that distal edge 212 of outer dilator 203 contacts wall 3). In FIG. 3E, outer dilator 203 is advanced further, up to the level of the wide profile 214 of outer dilator 203. It is noted that the advance in FIG. 3E shows the distal edge 212 of outer dilator 203 brought to the same longitudinal position as the distal-most profile of inner dilator 205. In some embodiments, a second (proximal) dilating stage of stepped dilator 1100 (that is, a portion of dilator 1100 of FIGS. 11A-11E comprising proximal tapering region 1117) is used for these operations; except that instead of advancing over an inner dilator, the proximal tapering region 1117 follows after distal tapering region 1121, and optionally after an intervening isolating region 1119, as described herein in relation to FIGS. 11A-11E.

FIGS. 3A-3D show first insertion of inner dilator 205, then outer dilator 203 over inner dilator 205. In some embodiments, outer dilator 203 is optionally used as the first inserted dilator (or insertion along with inner dilator 205), followed by puncture using trocar needle 203, dilation with the inner dilator 205 sliding distally from within outer dilator 203, and finally dilation with outer dilator 203 sliding distally over inner dilator 205. This provides a potential advantage, for example, in the location of a puncture target location for needle 207, which can be seen through the relatively open lumen of outer dilator 203 upon transillumination of the wall 3 of the rectouterine pouch 19. The difference in insertion order can also affect the arrangement of stoppers/indicating indexers (for example as described in relation to FIGS. 5A-5I) used to determine the relative distances of the different dilation components during insertion and/or dilation.

Optionally, the distal aperture 220 of outer dilator 203 is sized to fittingly accommodate the wide cross-section 219 of inner dilator 205. The outer perimeter at distal edge 212 may be just slightly larger than distal aperture 220 (i.e., distal edge 212 is optionally sharp). Optionally, distal edge 212 is blunt and/or rounded, for example, with an initial wall thickness (or diameter, in the case of a rounded edge) of, for example, about 100 μm, 200 μm, 500 μm, or 1 mm.

In some embodiments, the distance between distal edge 212 and wide profile 214 is about 15 mm. In particular, the distance is optionally any distance described in relation to the distance between the distal-most profile of inner dilator 205 and wide cross-section 219. Optionally, these two distances are about equal. Optionally, the distance for outer dilator 203 is slightly shorter (e.g., about 0.5 mm, 1 mm, or 1.5 mm shorter), which potentially reduces a possibility of injury due to tissue contact with distal edge 212. Optionally, a distance of advance of outer dilator 203 relative to inner dilator 205 is controlled by use of a stopper and/or indicating indexer, for example as described in relation to FIGS. 5A-5C herein.

Optionally, the longest axis of wide cross-section 214 is, for example, about 20 mm, 23 mm, 25 mm, 27 mm, 33 mm, or 35 mm. Optionally, the shortest axis of wide cross-section 214 is, for example, about 5 mm, 7 mm, 8 mm, 10 mm, 11 mm, or 13 mm. Optionally, the ratio between the longest axis and the shortest axis is, for example, about 1.5, 2 2.5, 3, or 3.5. The dimensional descriptions apply as well to slanted distal aperture 209 of cannula 201, 1010 and the internal lumen of cannula 201, 1010 which is sized to slide over outer dilator 203 in a fitting association (e.g., with a relative size tolerance of about 1 mm or less). The internal lumen of cannula 201, 1010 is sized to accept a plurality of (typically tubular, tube-sheathed and/or cylindrical) tools positioned side-by side, for example, two tools of 8 mm diameter or more and one tool of about 5-6 mm diameter or more. In some embodiments, the cross-sections of the cannula 201, 1010 and dilators 203, 205 are (for example as shown in FIGS. 2B and 5K) substantially rectangular with rounded ends (e.g., rounded so that the short sides are formed as sections of substantially circular arcs).

A rounded-end shape has a potential advantage for enclosing a plurality of side-by-side cylindrical tools, since it allows packing of the outermost tool sides toward the outside of the cross-section, while minimizing wasted corner space (the "waste" is not so much with respect to the cannula interior as it is with respect to the creation of a potentially larger-than-necessary incision hole). Round corners (as opposed to sharp corners) also provide a potential advantage during insertion, by helping to distribute forces which might otherwise tend to focus cutting toward the corners and lead, e.g. to less predictable dilation and/or incisions which heal more unpredictably. Between the arced ends, a straight line section (used in some embodiments) has the potential advantage of maintaining an outer profile suitable for staying in full peripheral contact with the dilated tissue surrounding it (e.g., to maintain a tension seal), without extra widening which would create space that the cylindrical tools within do not need to use. In some embodiments, there is a slight outward bowing introduced along the longer sides of the cross-sections (e.g., less than 1 mm of bowing per 5 mm of perimeter), potentially enhancing tension contacts between the dilators and/or cannula and the aperture edges of the tissue wall they penetrate.

In the examples illustrated herein (e.g., FIGS. 2B, 5K), the cross-sections of the dilators and cannula shown display mirror symmetry around both a long axis and a short axis. However, the cross-sectional shape, in some embodiments, need not have any particular symmetry arrangement, and can be otherwise shaped (e.g., as a round-cornered irregular triangle) to suit the accommodation of different-sized arrangements of tools.

In FIG. 3F, vaginal cannula 201 is shown with its distal-most edge 211 brought up to the position of wall 3. In FIG. 3G, cannula 201 is shown advanced into the rectouterine pouch 19, so that distal-most edge 211 is about even with the distal-most portion of outer dilator 203. FIG. 3H shows cannula 201 with inner dilator 203 and outer dilator 205 removed. Optionally, inner dilator 205 is removed at any time after outer dilator 203 is in place. Optionally, the two dilators 203, 205 are removed together.

In some embodiments, an inner lumen cross-section of cannula 201 is sized to fittingly slide over section of outer dilator 203 having the size of wide cross-section 214. Optionally advance of cannula 201 is performed by use of a handle 202. Optionally, the maximum advance of cannula 201 relative to outer dilator 203 is controlled by the use of a stopper and/or indicating indexer.

In some embodiments, the lumen of cannula 201 is about 7 cm, or another length long enough to reach between a distal-most position within the rectouterine pouch, and a proximal position at or outside the vaginal orifice (e.g., up to about 15 cm). Optionally, a flange 221 is provided at a proximal end of the lumen of cannula 201. While cannula 201 (with a handle 202, as next described) is shown in FIG. 3F-3I, it should be understood that the foregoing descriptions of cannula 201 also apply, in some embodiments, to the use of cannula 1010 of FIG. 10B.

Handle 202 of cannula 201 is long enough, in some embodiments, to extend past either of the dilators 203, 205 while they are inserted, and enough past to provide a grasping region (e.g., a grasping region of about 10 cm; overall length is optionally at least about 37 cm). In some embodiments, inner dilator 205 is at least long enough to reach its fully inserted position while providing a handle (e.g., about 17 cm overall), and outer dilator 203 is at least 10 cm longer again (e.g., about 27 cm overall).

Figure 3K:
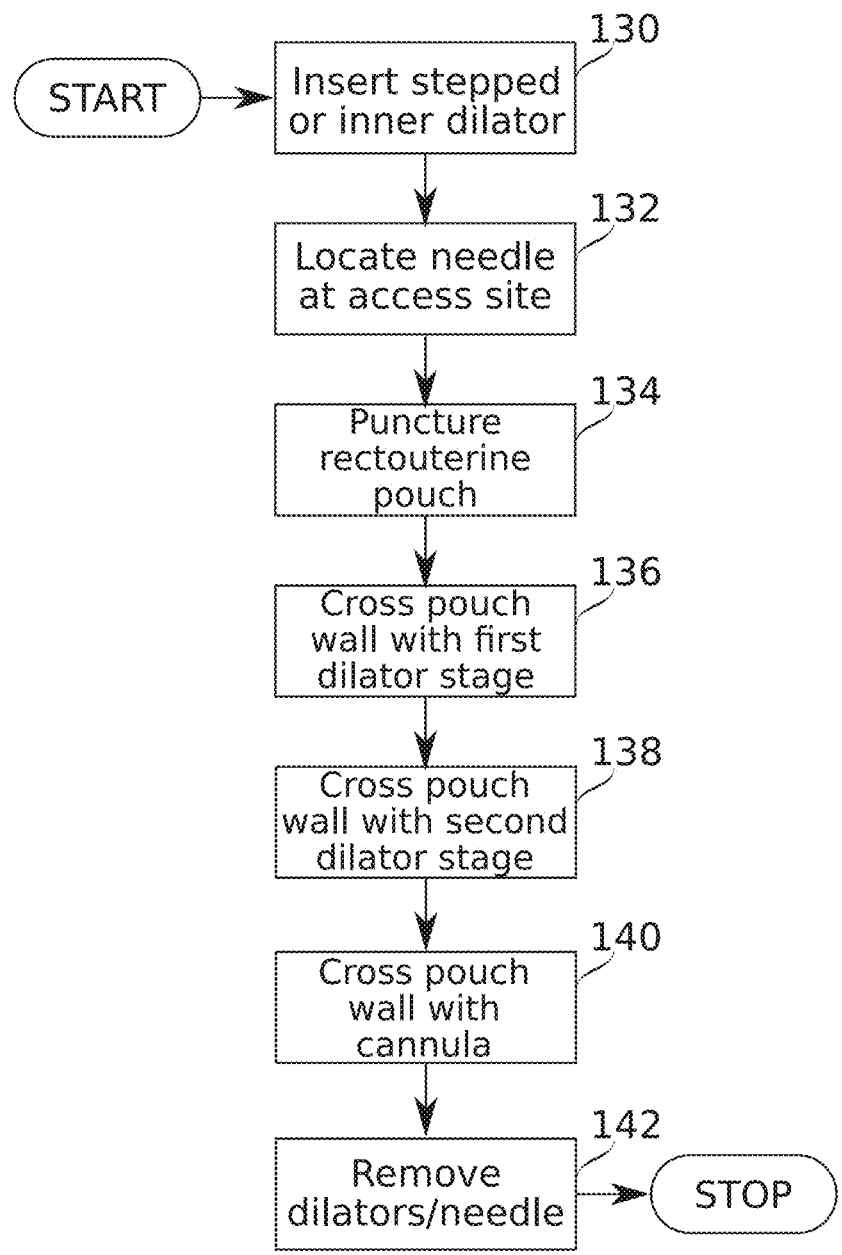
FIG. 3K is a schematic flowchart representing a method of dilating and cannulating an access incision into a rectouterine pouch, according to some embodiments of the present disclosure.
Figure 3L:
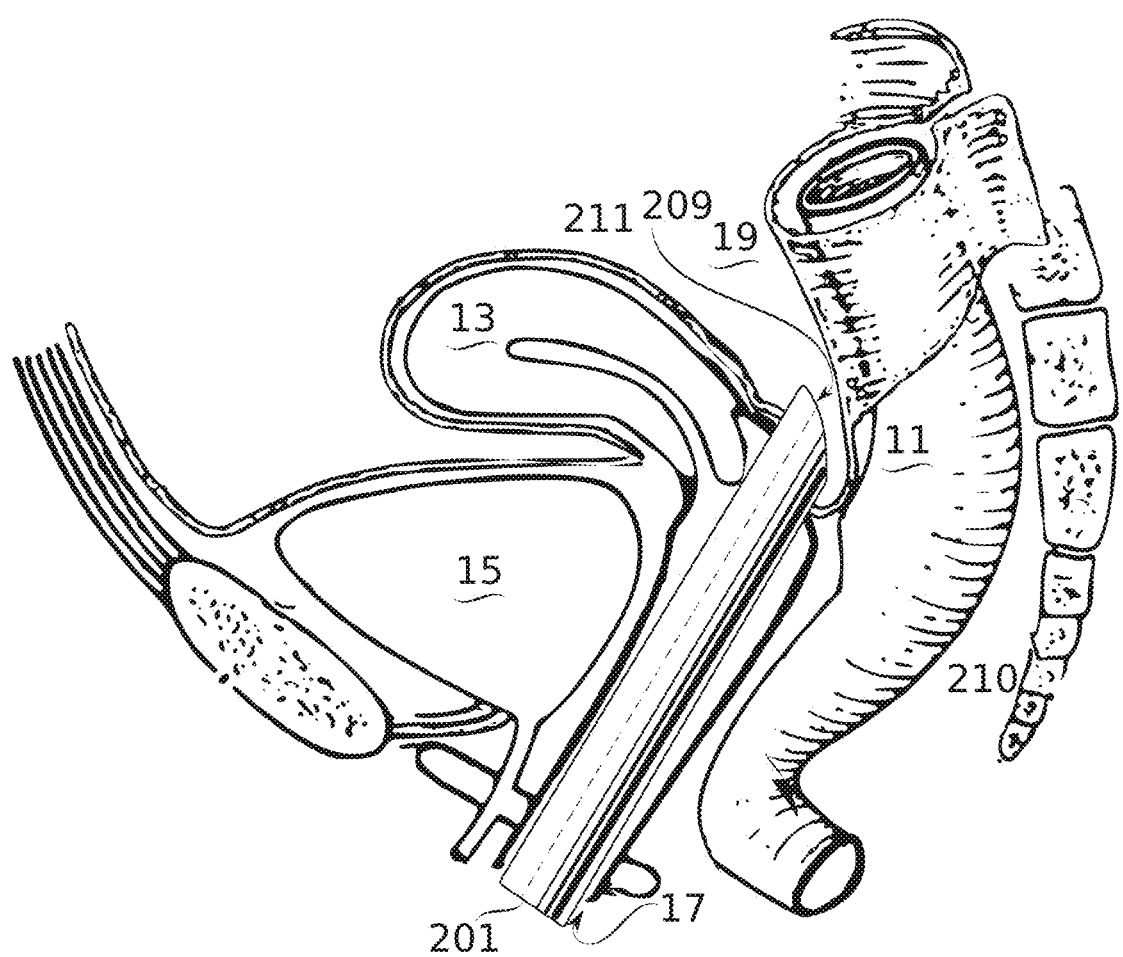
FIG. 3L schematically represents a wider view (compared to FIG. 3H) of the positioning of cannula relative to anatomical structures of a female lower abdomen/pelvic region, according to some embodiments of the present disclosure.

Reference is now made to FIG. 3L, which schematically represents a wider view (compared to FIG. 3H) of the positioning of cannula 201, 1010 relative to anatomical structures of a female lower abdomen/pelvic region, according to some embodiments of the present disclosure. Among the anatomical structures shown are the uterus 15, vagina 17, bladder 15, rectum 11, and rectouterine pouch 19, also shown as in FIG. 1. Not shown is the handle of cannula 201, 1010, and optional associated devices such as insufflation sealing which may be provided for, e.g., at the vaginal orifice, and/or a trocar part which may be telescopically fitted to extend the length of cannula 201, 1010.

In some embodiments, slanted distal aperture 209 of cannula 201, 1010 is slanted at an angle between a leading distal-most edge portion 211, and a following, more proximal edge portion 210. The longitudinal distance between distal-most edge portion 211 and proximal-most edge portion 210, in some embodiments, is about 15 mm. In some embodiments, the distance is, for example, about 10 mm, 12 mm, 14 mm, 16 mm, or 18 mm. A potential advantage of the slanting of distal aperture 209 is to allow the cannula edge to be relatively retracted on an unprotected side of the cannula which could otherwise be accidentally positioned to scrape the rectum 11. As for the more-protruding leading-edge side of the aperture 211: (1) upon insufflation, tissue is generally lifted away from the rectum, reducing contact risk posed by this side, and (2) the robotic arms, where they exit the cannula, will generally be curved across the plane of the leading edge as they reach deeper into the peritoneal space. This potentially prevents contact of the leading edge with delicate internal tissues. Robotic arm positions can be seen, for example, in FIGS. 7A-7B, herein.

Figure 7A:
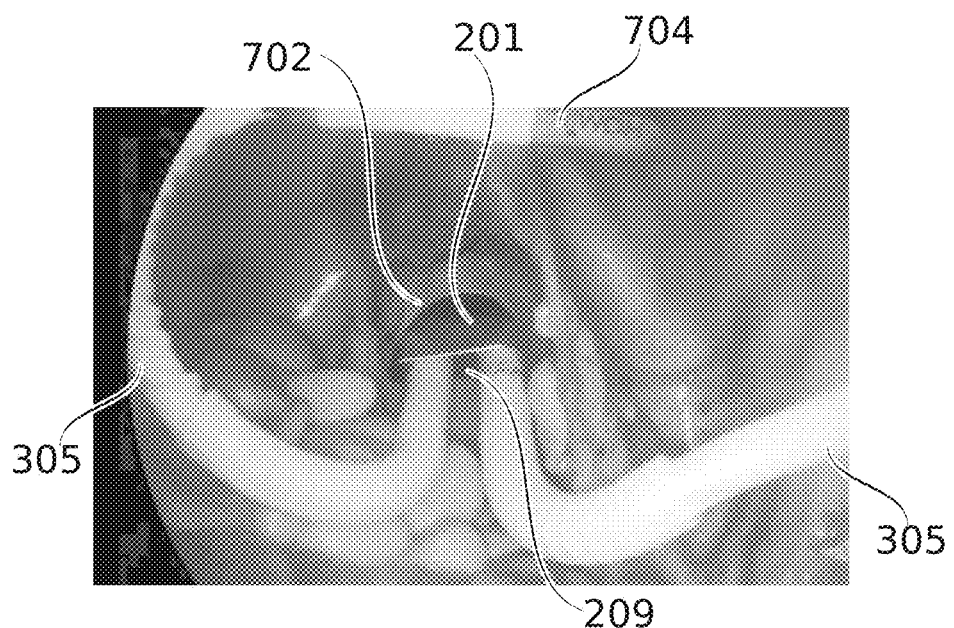
FIGS. 7A-7B are images taken from inside an insufflated abdomen of robotic arms inserted through the cannula in a configuration similar to that of FIG. 3I, according to some embodiments of the present disclosure.
Figure 7B:
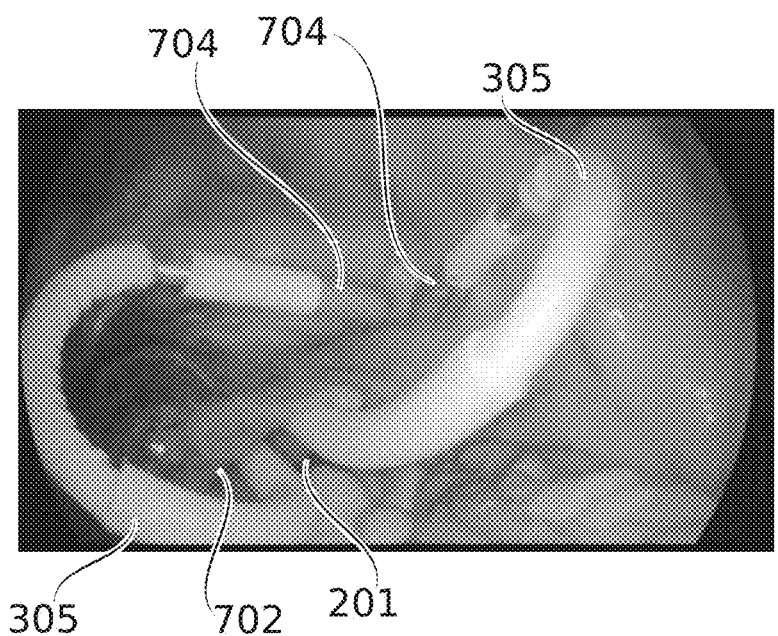

Reference is now made to FIG. 3I, which schematically represents the cannula configuration of FIG. 3H, along with inserted tools, according to some embodiments of the present disclosure. Reference is also made to FIGS. 7A-7B, which are images (from a viewpoint inside an insufflated abdomen) of robotic arms inserted through the cannula 201 in a configuration similar to that of FIG. 3I, according to some embodiments of the present disclosure. Descriptions in relation to FIGS. 3I and 7A-7B of cannula 201 also apply to cannula 1010 of FIG. 10B.

In FIG. 3I, the lumen of cannula 201 is shown occupied by two substantially cylindrical members, for example, robotic arms 305 (having diameter, for example, of about 8.6 mm), and another cylindrical (e.g., tubular) member comprising a tool 307 (for example, a laparoscopic illuminator, camera, clamp, cutter, and/or another tool). In some embodiments, the lumenal cross section of cannula 201 is sized to accommodate a plurality of substantially cylindrical members (e.g., robotic arms) each having a diameter of at least about 8 mm, and optionally another tool operated through a tube having a diameter of at least about 5 mm.

As shown in FIG. 3I, tools exiting the slanted distal aperture 209 of cannula 201 positioned within rectouterine pouch 19 are optionally oriented to curve downward from the aperture, into the rest of the peritoneal space where operations of a laparoscopic procedure are to be performed (for example, clipping ligaments in preparation for hysterectomy. Optionally, this orientation is assisted by the angled slot of distal aperture 209 described in relation to FIGS. 3F-3H, herein.

In FIGS. 7A-7B, robotic arms 305 include surgical tools 704 positioned on a distal end of each robotic arm 305. The robotic arms 305 are shown entering into an insufflated abdominal cavity from cannula 201 through slanted distal aperture 209. Also illustrated in the image is the dilated incision 702 through which cannula 201 has entered the abdominal cavity. Reference is now made to FIG. 3J, which is a schematic flowchart outlining preparation for a laparoscopic procedure using trocar 200, according to some embodiments of the present disclosure. The procedure shown represents a setup portion of a larger procedure (for example, a hysterectomy), including elements of the method described in relation to FIGS. 3A-3I.

Optionally, at block 110, in some embodiments, a laparoscopically mounted camera is inserted into the peritoneal space, for example from the umbilical. Optionally, the camera is provided together with an illumination source. Optionally, a separately mounted illumination source is also inserted from the umbilical.

At block 112, in some embodiments, the peritoneal space is insufflated, e.g., by inflating with $CO_2$. Insufflation is performed to enhance access and/or visibility during the procedure.

At block 114, in some embodiments, a sleeve is inserted transvaginally. The sleeve potentially helps to maintain insufflation pressure (pseudo-peritoneum) used for visualization and/or access during the rest of the procedure. The sleeve may be provided, for example, as an Alexis® nylon sleeve (Applied Medical Resources Corporation), or as part of a GelPOINT® path transanal access platform (Applied Medical Resource Corporation). In some embodiments, the sleeve is inserted at a later stage; for example just before attachment of a sealing unit at block 122.

At block 116, in some embodiments, a speculum is inserted to the vagina to assist in visualization (optionally or additionally, a tenaculum is used).

At block 118, in some embodiments, a uterine manipulator is inserted transvaginally to the uterus. The uterine manipulator may be, for example, a Karl Storz uterine manipulator. The uterine manipulator is used to move the uterus during the procedure, for example, to help provide maneuvering room for other instruments, and/or to help move the uterus away from the rectum to provide increased safety. If a tenaculum was used, the tenaculum may be removed at this point.

At block 120, in some embodiments, dilation and cannula introduction is performed, for example, as described in relation to FIGS. 3A-3G, FIG. 3K, FIGS. 6A-6E, and/or FIGS. 11A-11E herein. The speculum may be removed during dilation, for example if it begins to interfere with dilation, or afterward.

Figure 10A:
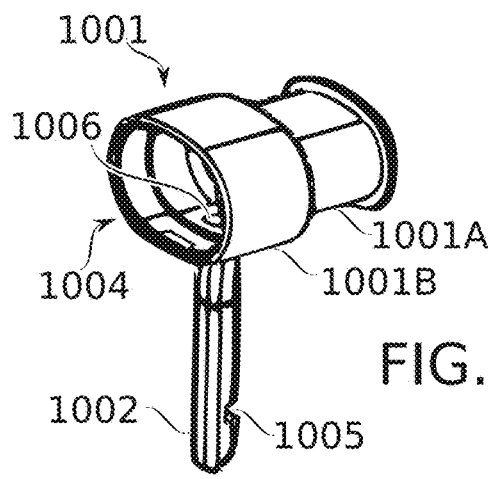
FIGS. 10A-10E schematically illustrate views representing a collapsing instrument holder for cannula and its configuration for use in setting an initial robotic arm position relative to cannula, according to some embodiments of the present disclosure.
Figure 10B:
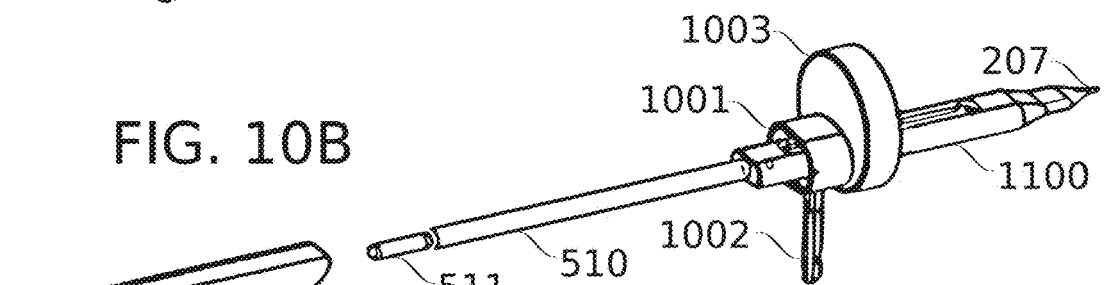
Figure 10C:
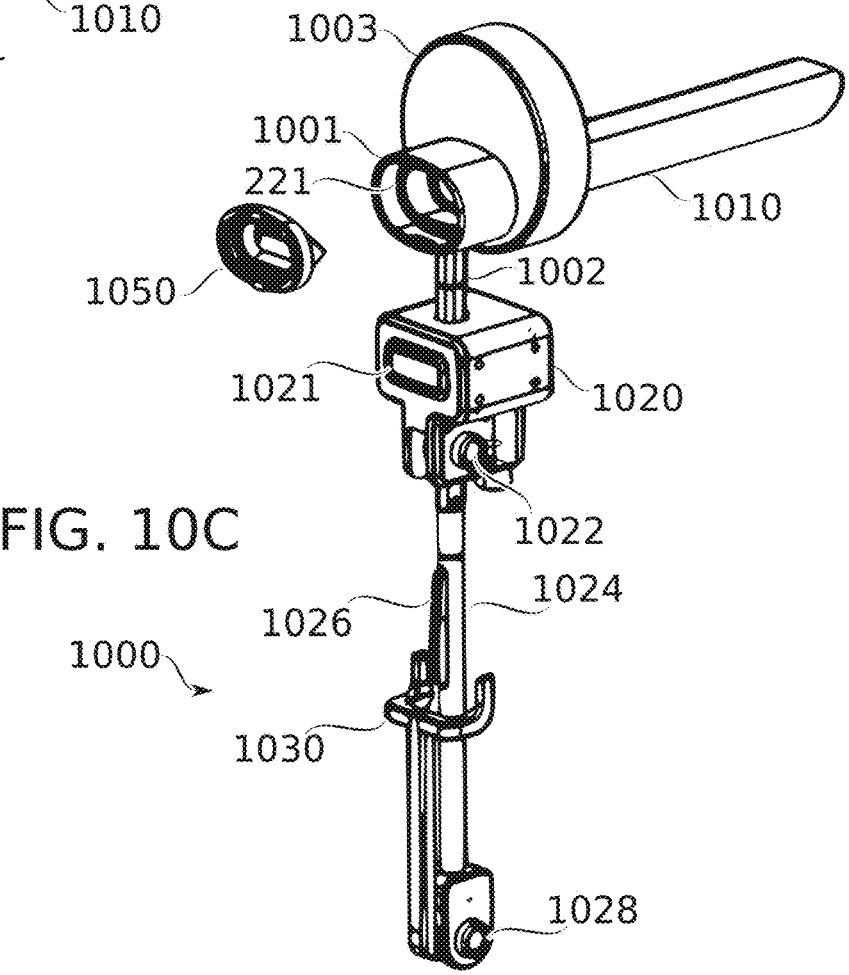

At block 122, in some embodiments, a sealing unit is attached to cannula 201 (or cannula 1010, for example as described in relation to FIGS. 10A-10C, herein). The sealing unit optionally comprises elements of a GelPOINT® system; optionally in combination with elements specifically adapted for use with cannula 201. Optionally, the uterine manipulator is re-positioned to pass through the sealing unit.

At block 124 in some embodiments, fixation is performed. Fixation comprises securing of the cannula and/or sealing unit to a platform which is stationary relative to the patient (e.g., an operating table).

At block 125, in some embodiments, one or more robotic arms are aligned to cannula 201, 1010 in preparation for introduction into cannula 201, 1010, for example as described in relation to FIGS. 9A-9D or FIGS. 10C-10J, herein.

At block 126, in some embodiments, one or more robotic arms and/or other tools are introduced through the cannula 201, 1010, for example as described in relation to FIG. 3H herein.

Reference is now made to FIG. 3K, which is a schematic flowchart representing a method of dilating and cannulating an access incision into a rectouterine pouch, according to some embodiments of the present disclosure. In some embodiments, the method of FIG. 3K details operations of block 120 of FIG. 3J.

The method is outlined briefly. Additional details for the operations of FIG. 3K are described in relation to FIGS. 3A-3G, herein.

At block 130, in some embodiments, inner dilator 205 (alternatively, in some embodiments, stepped dilator 1100 of FIGS. 11A-11E) is inserted transvaginally to reach a wall 3 of the rectouterine pouch 19 (for example as described in relation to FIG. 3A). At block 132, in some embodiments, a tip of a needle (inserted through inner dilator 207) is located at the site where an access incision is to be made (for example, as detailed in relation to FIG. 4). At block 134, in some embodiments, the rectouterine pouch is punctured (for example, as described in relation to FIG. 3B). At block 136, in some embodiments, the pouch wall 3 is crossed with the first dilator stage, for example, a tip of inner dilator 205 (for example as described in relation to FIG. 3C). Alternatively, in some embodiments, pouch wall 3 is crossed with a first (distal) dilating stage of stepped dilator 1100. At block 138, in some embodiments, the pouch wall 3 is crossed with a second dilator stage, for example, the outer dilator 203 (for example, as described in relation to FIGS. 3D-3E). Alternatively, in some embodiments, pouch wall 3 is crossed with a second (proximal) dilating stage of stepped dilator 1100. At block 140, in some embodiments, the pouch wall is crossed with cannula 201, 1010 (for example, as described in relation to FIGS. 3F-3G). At block 142, in some embodiments, the dilators 203, 205 and/or trocar needle 207 are removed, and the flowchart ends.

Figure 4:
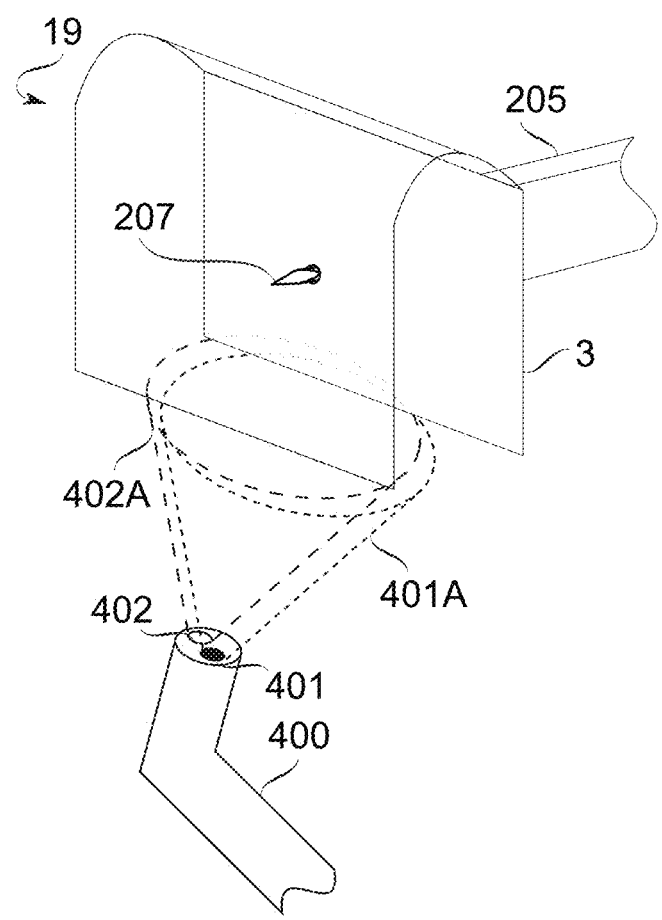
FIG. 4 schematically represents a dual-verification method of locating an incision for providing transvaginal access to a rectouterine pouch, according to some embodiments of the present disclosure.

Reference is now made to FIG. 4, which schematically represents a dual-verification method of locating an incision for providing transvaginal access to a rectouterine pouch 19, according to some embodiments of the present disclosure.

Shown in FIG. 4 is a schematic representation of rectouterine pouch 19, including a vaginal wall 3 of the rectouterine pouch 19, approached by an inner dilator 205, with a trocar needle 207 partially extended. Also shown are an intraperitoneally inserted (e.g., from the umbilical) camera 402 and an illumination source 401. Camera 402 and illumination source 401 are shown on the same laparoscopic instrument 400; optionally they are separately provided. Camera 402 has an associated field of view 402A, while illumination source 401 has an associated illumination field 401A.

In some embodiments, the tip of needle 207 is positioned before puncture against a region of wall 3, wherein the region selected based on external observation of light from illuminator 401 visible from outside (e.g., as viewed transvaginally, optionally using the speculum and/or uterine manipulator to increase visibility). Optionally, the region selected is a region through which trans-illumination light intensity is observed to be relatively large compared to surrounding regions. Such well trans-illuminated wall areas are potentially among the thinnest, most easily penetrated portions of wall 3 accessible to needle 207.

In some embodiments, as needle 207 is pressed against wall 3 to puncture it, camera 402 is used to visualize the results. In the camera images, for example, there may be initially a protrusion, other tissue distortion, and/or other change (e.g., a color change due to pressure on the tissue) visible at the site of penetration (e.g., a distortion visible from a side of wall 3 opposite a side contacting the needle), and afterwards the needle itself may become visible. Optionally, the visualization helps to verify that the intended region is being penetrated (e.g., that the region being penetrated is suitable to provide intraperitoneal access), and/or to help identify and/or prevent imminent rectal puncture or another insertion mistake. By using visual cues that communicate across the rectouterine wall 3, even before the wall 3 itself has been punctured, complications may potentially be avoided.

Figure 5A:
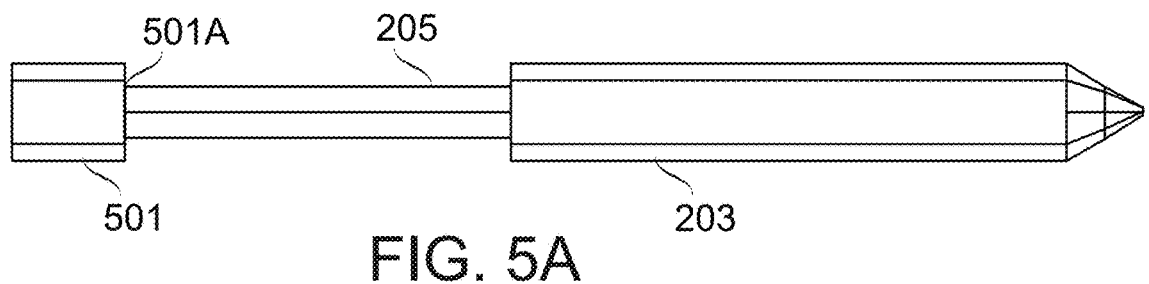
FIGS. 5A-5C schematically represent different stopper mechanisms for use with trocar components, according to some embodiments of the present disclosure.
Figure 5B:
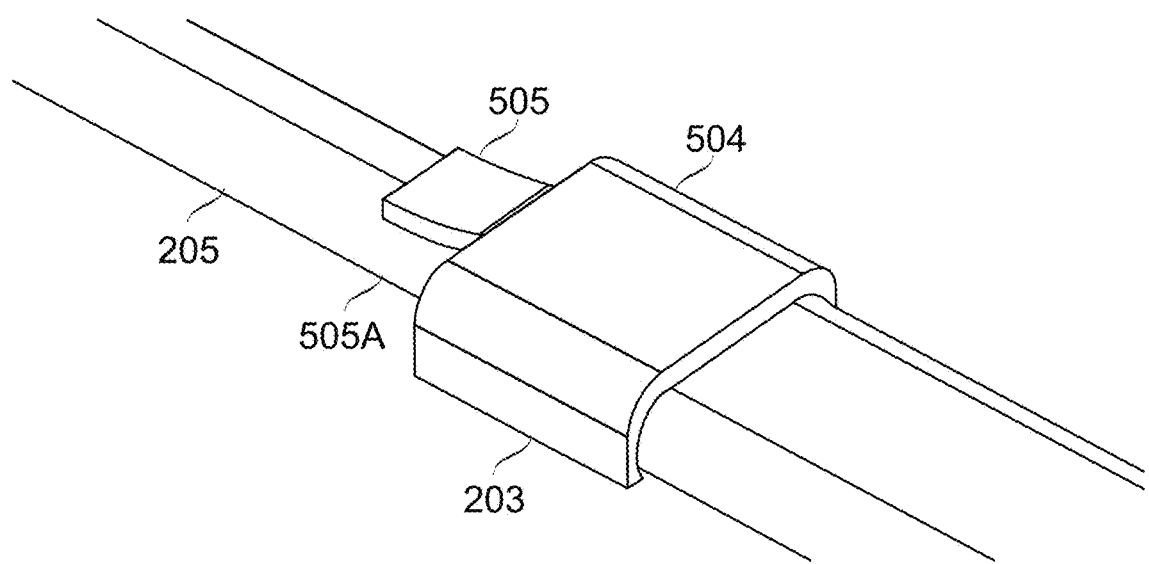
Figure 5C:
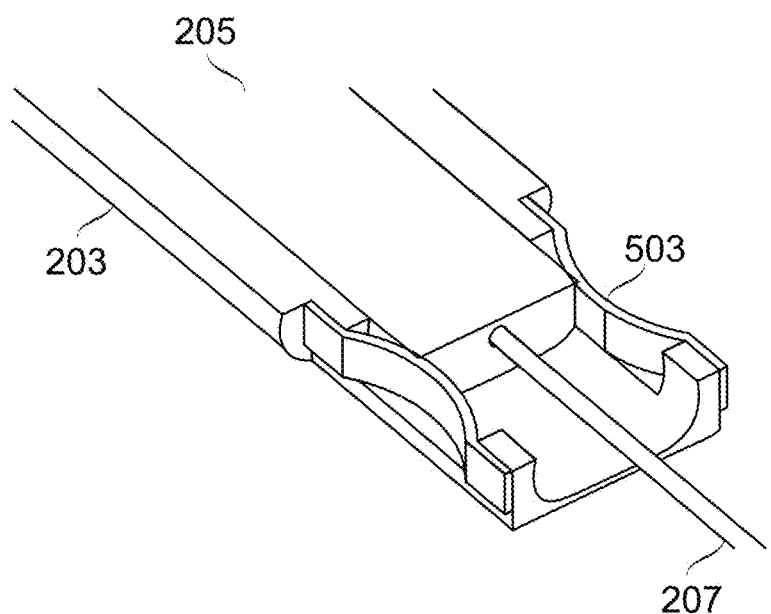

Reference is now made to FIGS. 5A-5C, which schematically represent different stopper and/or movement interference devices for use with trocar components 200, according to some embodiments of the present disclosure.

FIG. 5A illustrates a stopper-and-shoulder type of stopper device. In this embodiment, outer dilator 203 is inserted first, or along with inner dilator 205. The view of FIG. 5A cuts away a portion of outer dilator 203 so that the connection between inner dilator 205 and proximal stopper 501 can be seen.

Proximal stopper 501 is positioned along inner dilator 205 at a position where surface 501A is brought into abutment with a proximal surface (cut-away in FIG. 5A) of outer dilator 203 at the position where inner dilator 203 is as far distal relative to outer dilator 205 as it should be allowed to go (e.g., with a distal-most portion of inner dilator 205 positioned 15 mm in advance of a distal-most portion of outer dilator 203). Then, when it is the turn of outer dilator 203 to be advanced, the distance between surface 501A and the proximal surface of outer dilator 203 can be measured to determine the advance distance. Optionally another stopper device (for example, that of FIGS. 5B and/or 5C) prevents and/or indicates distal over-advancement of outer dilator 203 relative to inner dilator 205.

FIG. 5B illustrates a leaf-spring based stopper and/or motion interference device. The device comprises a bracket 504 attached to a distal portion of outer dilator 203, which in turn supports a leaf spring 505 configured to press down onto the body of inner dilator 205. This interaction optionally is set to a force sufficient to retard free sliding (e.g., due to gravity) of the inner dilator 205 relative to the outer dilator 203.

Optionally, inner dilator 205 comprises a receiving shape 505A (hidden by leaf spring 505) which is positioned to contact leaf spring 505 and interfere with further longitudinal movement of outer dilator 203 relative to inner dilator 205. The stopper device may be used to prevent over-advancement of either or both of inner dilator 205 and outer dilator 203 with respect to one another. There may be a plurality of different receiving shapes 505A, allowing different positioned to be noted. Though referred to as a "stopper", the stopper device of FIG. 5B is optionally configured using shapes and/or surface friction that interfere to resist, rather than completely prevent further longitudinal motion. The stopper device of FIG. 5B in such embodiments may be alternatively described as an indicating indexer. Optionally, the indicating indexer indicates relative dilator positions by the positions from which further longitudinal movement is resisted, and/or positions at which the two dilators click into place (as indicated through audible and/or tactile feedback).

The interfering occurs at one or more relative longitudinal positions of the two dilators 203, 205, for example, when the two are positioned with their distal-most portions in alignment, as shown in FIG. 3E. Receiving shape 505A may comprise, for example, an inset portion into which leaf spring 505 falls when the two parts are aligned. Additionally or alternatively, receiving shape 505A comprises a raised portion. In this case, a lumen of outer dilator 203 may be shaped to pass over the raised portion of receiving shape 505A until leaf spring 505 encounters it. Alternatively, lumen of outer dilator 203 may be shaped to prevent passage of the receiving shape, so that it also acts as a type of stopper-and-shoulder arrangement. It should be understood that although the device is illustrated with respect to two nested dilators, it may alternatively or additionally be implemented between a cannula and a dilator.

FIG. 5C represents a different leaf-spring based stopper device. In this example, there are optionally provided be a plurality of leaf springs 503 mounted to the body of outer dilator 203. Somewhere along its length, inner dilator 205 has a receiving shape (not shown), which comprise an indentation and/or a raised portion that contacts leaf spring 503 at a certain relative longitudinal position of the two dilators 203, 205; for example, when the two are positioned with their distal-most portions in alignment, as shown in FIG. 3E. The leaf spring device of FIG. 5C can be placed in any suitable location along the body of outer dilator 203, but preferably in a location that remains outside body cavities during use. There may be a plurality of such devices provided on outer dilator 203, and/or a plurality of receiving shapes provided on inner dilator 205. Optionally, the leaf spring device is provided on inner dilator 205, and the outer dilator provided with the appropriate receiving shape(s).

In some embodiments, a stopper and/or motion interference device replaces the leaf spring with another mechanism. For example, in some embodiments, a plunger is provided (e.g., a spring-loaded pressing member such as a ball bearing, for example as described in relation to FIGS. 8A-8B). The plunger presses down to hold two nested parts in relative position (e.g., two dilators; dilator and cannula), and/or indicate that a particular relative position has been reached, by force of friction and/or by interference between the plunger and one or more stopper/indicating indexing shapes—and/or by release of such interference and/or friction.

Figure 5D:
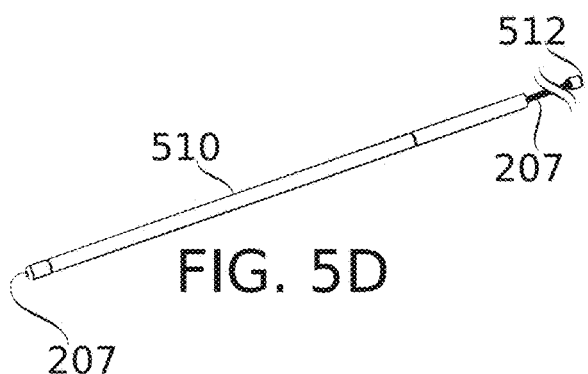
FIGS. 5D-5F schematically illustrate a needle, needle holder, and needle handle, according to some embodiments of the present disclosure.
Figure 5E:
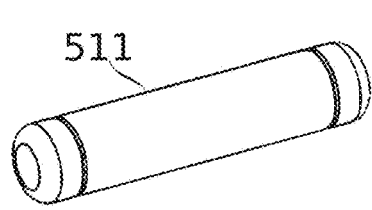
Figure 5F:
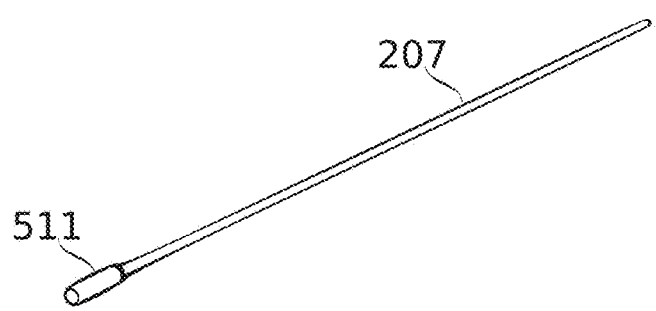

Reference is now made to FIGS. 5D-5F, which schematically illustrate a needle 207, needle-passing dilator handle 510, and needle handle 511, according to some embodiments of the present disclosure.

In FIG. 5D, needle 207 is shown partially inserted within the hollow body of dilator handle 510. Optionally, dilator handle 510 serves as a handle for inner dilator 205; e.g., attached via a screw thread or other attachment means. Proximal end 512 of needle 207 is adapted to attach to needle handle 511 of FIG. 5E, for example as shown in FIG. 5F. In some embodiments, the relative lengths of needle 207 and dilator handle 510 (and the relative position of handle 511 on needle 207) are configured to help control the maximum distance of distal advance of needle 207 relative to inner dilator 205, for example as described in relation to FIGS. 5G-5I.

Figure 5G:
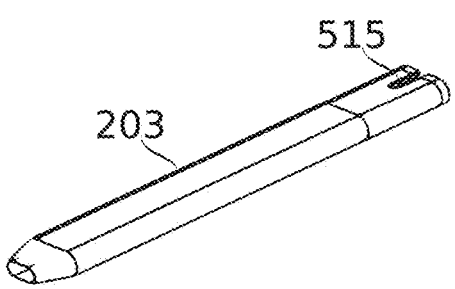
FIGS. 5G-5I schematically illustrate mechanisms for controlling the relative positioning of an inner dilator, outer dilator, and needle according to some embodiments of the present disclosure.
Figure 5H:
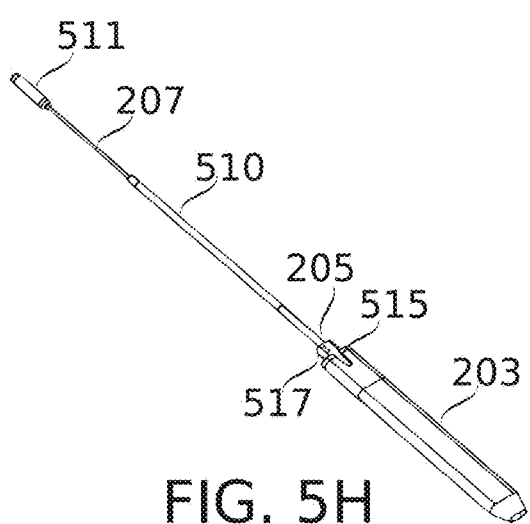
Figure 5I:
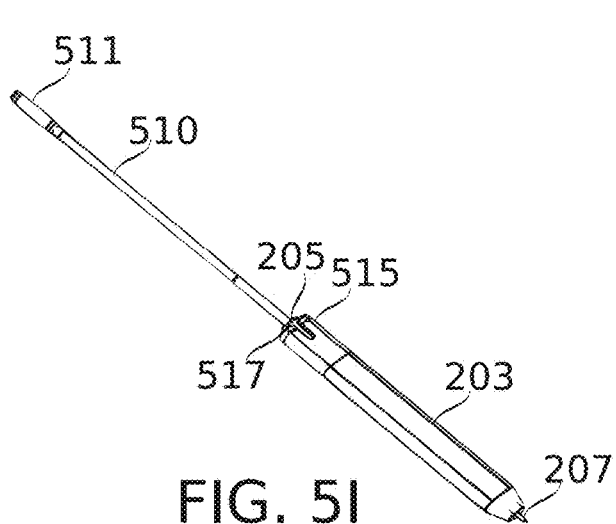
Figure 8A:
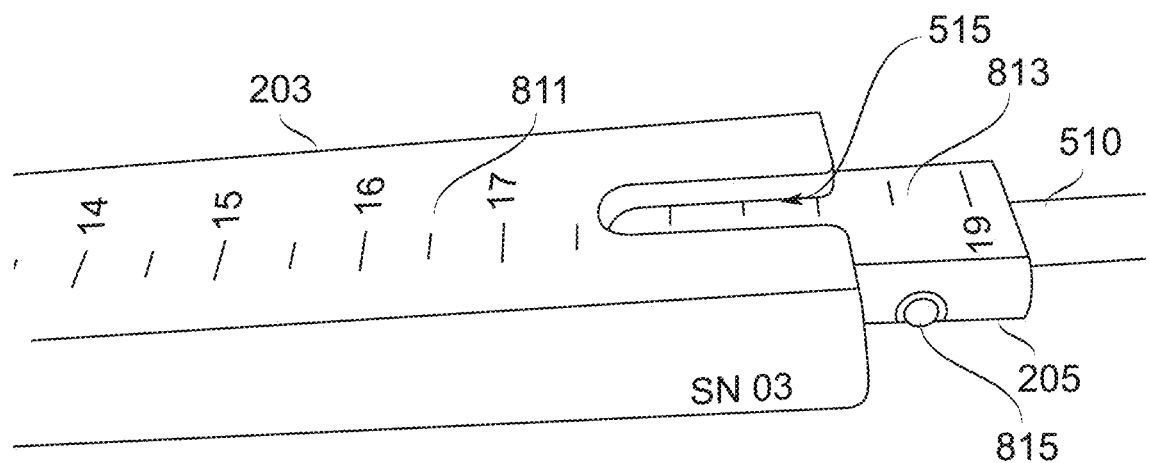
FIGS. 8A-8B illustrate scale features of outer dilator and inner dilator, according to some embodiments of the present disclosure.
Figure 8B:
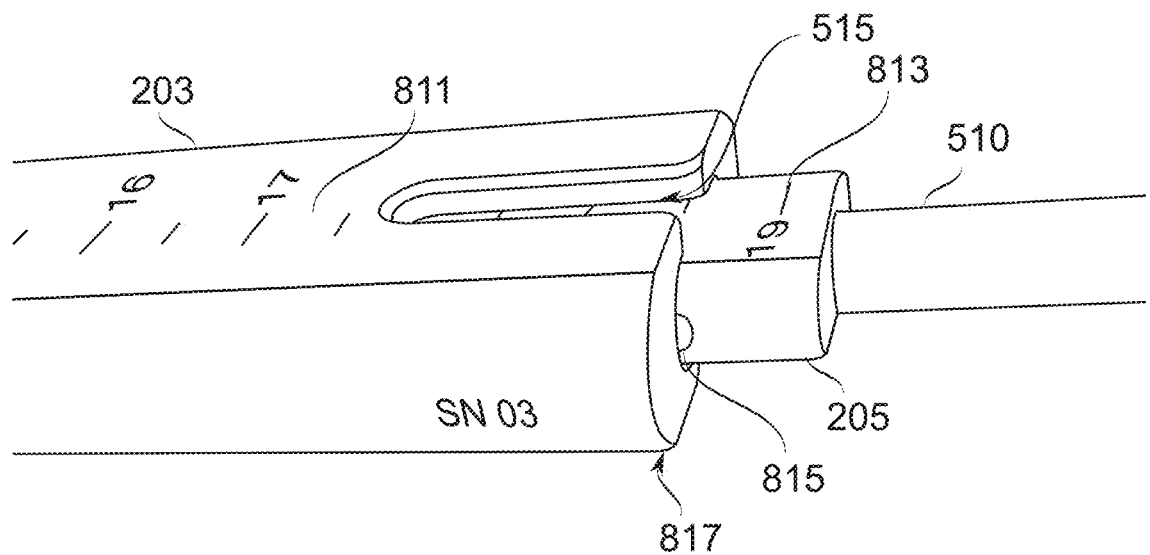

Reference is now made to FIGS. 5G-5I, which schematically illustrate devices for controlling the relative positioning of inner dilator 205, outer dilator 205, and needle 207 according to some embodiments of the present disclosure. Reference is also made to FIGS. 8A-8B, which illustrate scale features of outer dilator 203 and inner dilator 205, according to some embodiments of the present disclosure.

In FIG. 5G and FIGS. 8A-8B, outer dilator 203 is shown provided with an integrated scale window 515. Scale window 515 optionally comprises at least one reference mark alongside a longitudinal window formed in a portion (e.g., cut into a proximal end) of outer dilator 203. In some embodiments, outer dilator 203 is used to define a reference position allowing inference of the current position of the wall 3 of rectouterine pouch 19. Outer dilator can be inserted as far as it will easily pass. Since it is too blunt to puncture wall 3, it will normally be brought to a halt with its distal-most end abutting wall 3. This can be verified by viewing using a speculum, for example.

In some embodiments, a distance scale is marked (e.g., in centimeters from the distal end) on one or both of the inner dilator 205 and outer dilator 203, for example, scale 811 of the outer dilator 203, and scale 813 of the inner dilator 205 (FIGS. 8A-8B).

Also illustrated in FIGS. 8A-8B is ball-stop device 815, which is an example of an indicating indexer. In some embodiments, ball stop device 815 comprises a spring-loaded ball bearing, configured to protrude outwards from near a proximal end of inner dilator 205 under elastic pressure. The lumen of outer dilator 203 is sized so that it can be pushed over and then slide forward along ball-stop device 815. The ball of ball-stop device 815 is pushed inward during this motion. It acts (by continuing to press outward) to help center outer dilator 203 over inner dilator 205, and optionally to resist spontaneous relative translation (sliding) of the two dilators (e.g., due to the weight of outer dilator 205). Upon sufficient advance of outer dilator 203, ball-stop device 815 is freed from the proximal side of outer dilator 203, potentially inducing a tactile and/or audible click, and/or causing changes to the mechanical handling of the dilators 203, 205 which indicate to a user that outer dilator 203 has been fully advanced. Optionally, outer dilator 203 comprises one or more indentations and/or bumps along its lumen at positions which change the force with which the ball-stop device 815 interferes with relative longitudinal translation of the dilators 203, 205. It should be understood that the ball-stop device 815 may alternately be provided on the outer dilator 203 at a position where it interacts while sliding with the inner dilator 205 (and optionally bumps and/or indentations thereof). An indicating indexer is optionally provided for indication and/or control of relative longitudinal positions of other pairs of elements of the trocar kit; for example, between inner dilator 205 and needle 207, and/or between outer dilator 203 and cannula 201, 1010. In some embodiments, a ball stop is provided which controls relative motion between stepped dilator 1100 and cannula 201, 1010 when locked. In some embodiments, a ball stop is provided which controls relative motion between cannula 1010 and an access device 1001 (FIG. 10A) when locked.

In FIG. 8B, the ball stop device 815 is shown still compressed by outer dilator 203. In FIG. 8A, the ball stop device is free of compression. Once the ball-stop device 815 is free of compression, the ball is pressed outward to the full extent of its travel, resulting in an increased resistance (upon contacting a proximal surface 817 of outer dilator 203) to accidentally pushing inner dilator 205 distally relative to dilator 203.

In FIG. 5H, inner dilator 205 is shown partially inserted into outer dilator 203. Scale markings 517 on inner dilator 205 allow monitoring of the distal advance of inner dilator 205 relative to outer dilator 203, e.g., to a position distally even with the distal end of outer dilator 203 (in preparation for needle puncture), and/or to a position a few millimeters (e.g., 15 mm) distally in advance of outer dilator 205 during initial dilation.

Also in FIG. 5H, needle 207 is shown still only partially advanced with respect to handle 510 and the dilators 203, 205. In some embodiments, dilator handle 510 fits (e.g., screws into) to a socket in inner dilator 205, holding it at a predetermined distance from the distal end of inner dilator 205.

In FIG. 5I, the relative positions of components shown is as may occur immediately after needle 207 punctures the wall 3 of the rectouterine pouch 19.

The distal-most end of inner dilator 205 has been brought forward even with the distal-most end of outer dilator 203, as monitored from the relative positions of scale window 515 and markings 517. Handle 511 has been pushed forward so that it abuts a proximal end of dilator handle 510, preventing further advancement of needle 207. Lengths of needle 207, inner dilator 203, and dilator handle 510 are set so that needle 207 now protrudes from the front of inner dilator 203 by a predetermined amount which has been determined to fall within the range of distances which are enough to penetrate a wall 3 of a rectouterine pouch 19, but avoid risk of also penetration a wall of the rectum 11.

Optionally, the distal-most end of inner dilator 205 remains longitudinally offset from (e.g, distal to) the distal-most end of outer dilator 203 by some distance to control the maximum advance of needle 207. Optionally, maximum advance of needle 207 relative to inner dilator 205 is performed first, before advance to penetrate wall 3. This provides a potential advantage for allowing marked relative positions of window 515 and scale 517 to indicate the distance of needle advance in detail.

During dilation, in some embodiments, distal advance of outer dilator 203 relative to inner dilator 205 potentially disrupts the longitudinal frame of reference that outer dilator 203 initially establishes. In some embodiments, the frame of reference is maintained by clamping inner dilator 205 into place once it has advanced into the rectouterine pouch.

Reference is now made to FIG. 5K, which illustrates a manufactured example of a dilation and cannulation kit comprising members described and illustrated in, for example, FIGS. 3A-3I and 5D-5I, according to some embodiments of the present disclosure. Items are to scale with each other, and shown along their total length, with the exception of needle 207, which has been truncated on the right hand (sharpened, distal) side. Illustrated, from top to bottom, are:

Needle 207 including handle 511,

Cannula 201, including handle 202 and slanted distal aperture 209, comprising proximal edge portion 210 and distal-most edge portion 211.

Outer dilator 203, including scale window 515, distal edge 212, tapering region 213, and the wide profile 214 at the proximal side of tapering region 213.

Inner dilator 205, including distal port 216 positioned in blunt tip 215, tapering region 218, and the wide cross-section 219 at the proximal side of tapering region 218.

Dilator handle 510, which may optionally be attached to (e.g., screwingly attached to) inner dilator 205 to serve as a proximal-side handle thereof.

Reference is now made to FIGS. 6A-6E, which schematically represent dilation using a single dilator trocar kit, according to some embodiments of the present disclosure.

Figure 6A:
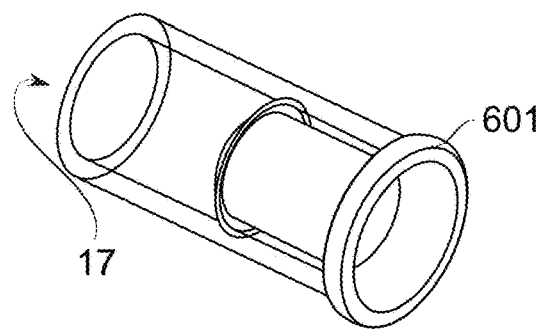
FIGS. 6A-6E schematically represent dilation using a single dilator trocar kit, according to some embodiments of the present disclosure.
Figure 6B:
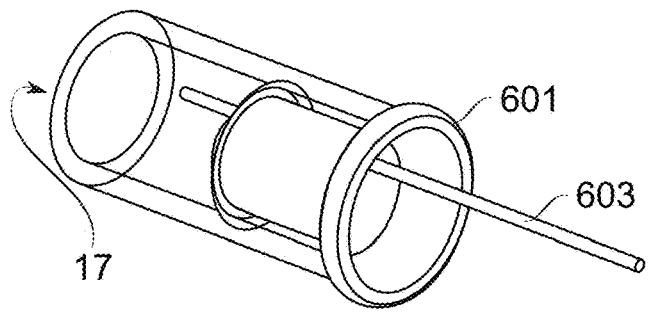
Figure 6C:
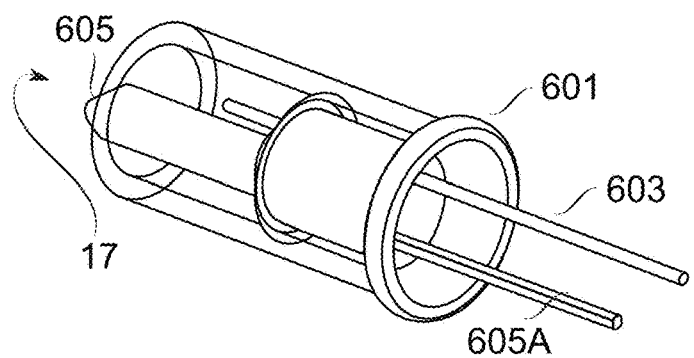

FIG. 6A shows a schematic representation of a body cavity (e.g., a vagina 17), together with an access device 601 which is optionally used, e.g., to help maintain insufflation pressure. In FIG. 6B, a uterine manipulator 603 is optionally added (shown incompletely inserted), potentially allowing maneuvering to increase visibility of the trocar target region (which may be a wall 3 of a rectouterine pouch 19, not shown). In FIG. 6C, cannula 605 (optionally constructed as described herein in relation to cannula 201 or cannula 1010) is inserted to the target region. Cannula 605 comprises a handle 605A to allow maneuvering of the lumen region of the cannula 605.

Figure 6D:
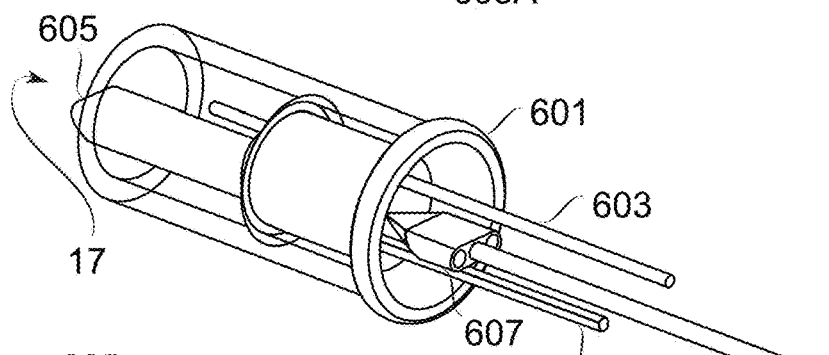

In FIG. 6D, a dilator 607 is being inserted to cannula 605, optionally using handle 607A. The tip of dilator 607 is optionally shaped to begin at its distal-most longitudinal position with a cutting tip. Alternatively, the tip of dilator 607 is blunted (shaped, for example, like that of inner dilator 205). Optionally, dilator 607 allows for passage distally of a trocar needle via an aperture. Optionally, initial puncture is made separately by a needle, e.g., passed into the lumen of cannula 605 (not shown), and dilator 607 inserted afterward.

In some embodiments, the tip of dilator 607 expands to any appropriate cross-sectional size; for example, any cross-section described in relation to wide cross-section 219. Optionally, the longitudinal distance between distal-most position and the tip cross-section of greatest expansion is about 15 mm or any other suitable distance; for example, as descried in relation to dilator tips of dilators 203, 205. Relative to use of two or more dilators, one-step dilation over the same maximum dilator tip distance is potentially simpler from the point of view of component exchanges and manipulations. There is a potential tradeoff, however, of increased penetration length (e.g., if expansion angle is maintained), and/or (e.g., if expansion angle is increased) of increased resistance to penetration.

Figure 6E:
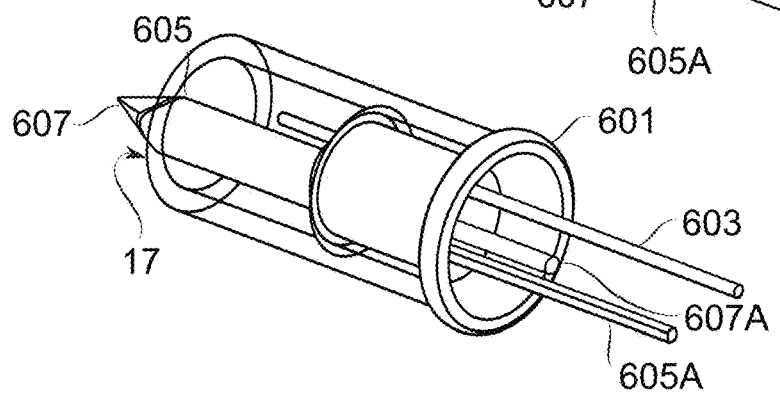

In FIG. 6E, the tip of dilator 607 is shown maximally advanced, with dilation complete. To complete trocarization, the cannula 605 may now be advanced through the dilated aperture, and the dilator 607 removed.

Figure 5J:
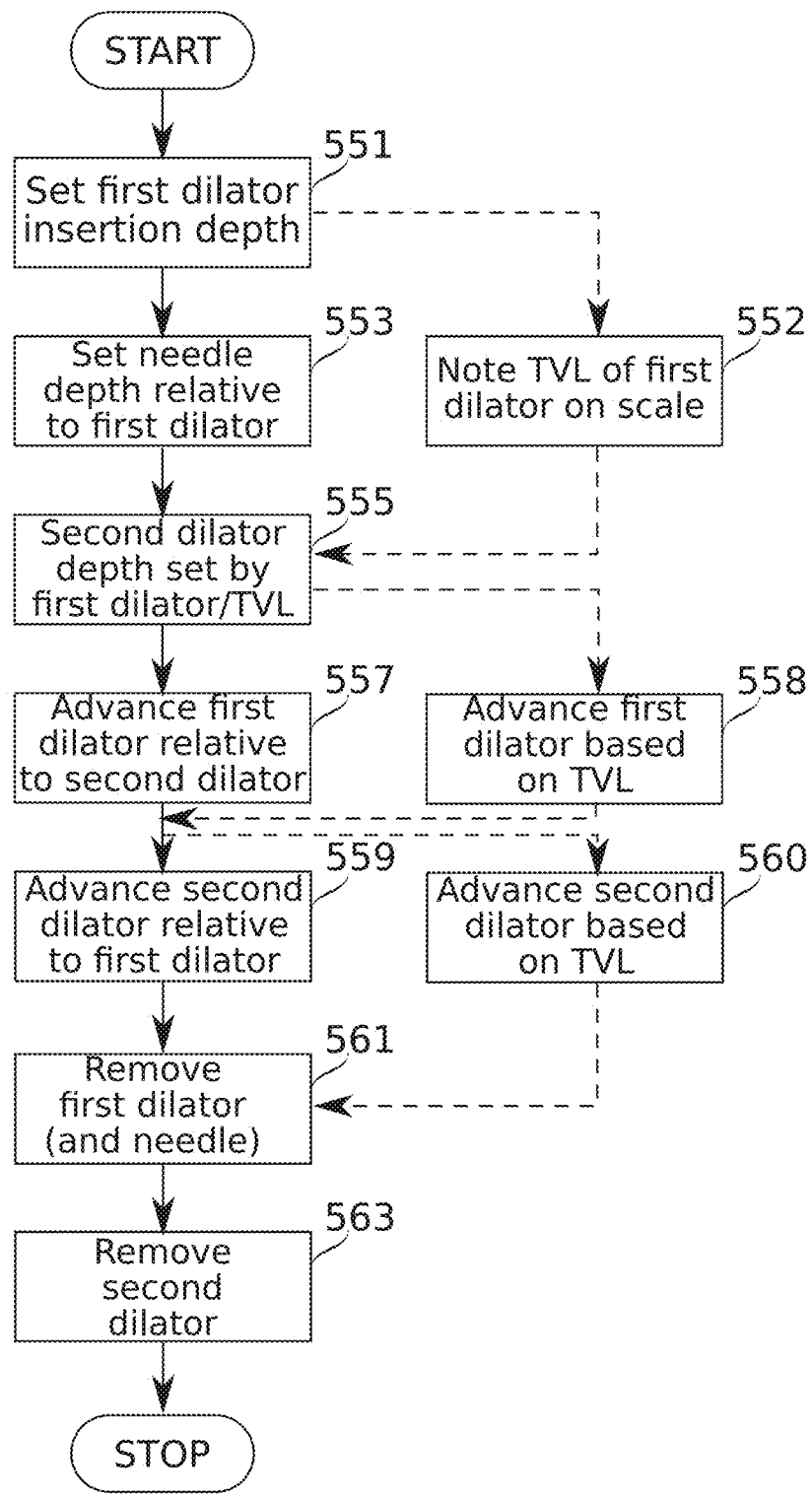
FIG. 5J is a flowchart schematically outlining a method of using indicators to establish and maintain known penetration depths of the trocar needle, dilator, and/or cannula parts, according to some embodiments of the present disclosure.
Figure 5K:
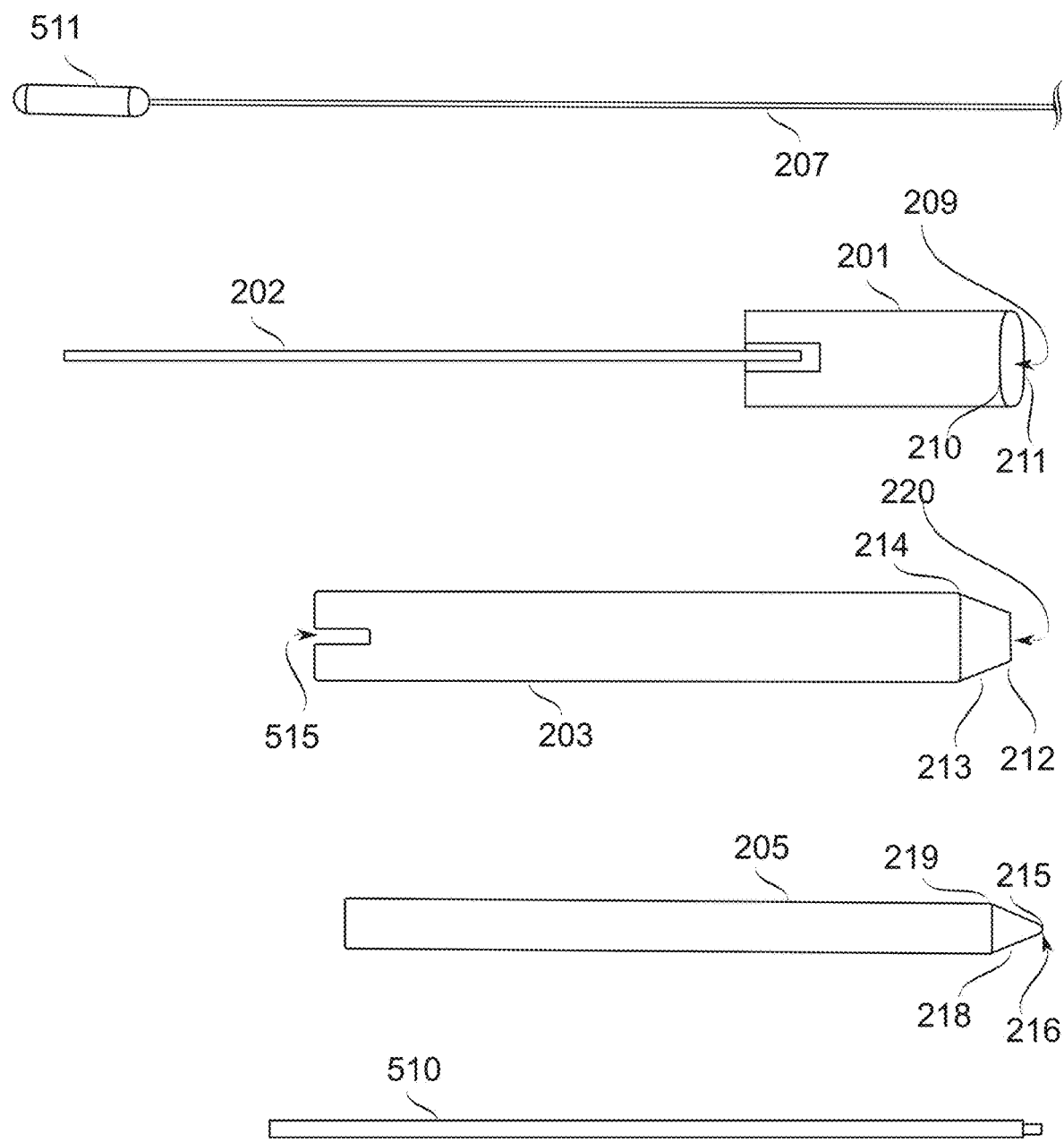
FIG. 5K illustrates a manufactured example of a dilation and cannulation kit comprising members described and illustrated in, for example, FIGS. 3A-3I and 5D-5I, according to some embodiments of the present disclosure.

Reference is now made to FIG. 5J, which is a flowchart schematically outlining a method of using indicators to transitively establish and maintain known insertion depths of the trocar needle 207, dilator 203, 205, and/or cannula 201, 1010 parts, according to some embodiments of the present disclosure.

At block 551, in some embodiments, a first dilator (e.g., inner dilator 205) is brought into position with its blunt tip against the outer wall of the rectouterine pouch. This position may be established, for example, by direct visualization (e.g., using a speculum), by noting where insertion resistance is encountered, and/or indirectly, e.g., by shining a light through the dilator lumen, and monitoring the projected light spot (e.g., the position where the spot reaches its smallest, most sharply defined shape) through the rectouterine pouch wall using a camera positioned inside the intraperitoneal space. Optionally, the first dilator is held clamped in position, e.g., by a table-attached clamping arm. Optionally, at block 552, the depth of penetration relative to the natural orifice opening is noted, providing a total vaginal length (TVL) which may be used separately from the transitive method of establishing trocar component positions, and/or to verify insertion depths set by the transitive method.

At block 553, in some embodiments, a trocar needle 207 is inserted into dilator 205, e.g., via holder 210. Insofar as holder 210 is itself sized to insert to a predetermined longitudinal position relative to the first dilator, the amount of visible shaft of trocar needle 207 optionally provides an indication of where the needle tip is positioned relative to the distal end of the first dilator. This can be used to control an advancing distance of trocar needle 207, optionally along with a stopper device (such as a shoulder stopper) that prevents over-advancement of the trocar needle 207. Optionally, the needle remains in place at least until the first dilator is advanced over it.

At block 555, in some embodiments, a second dilator (e.g., outer dilator 203) is advanced over the first dilator until a part of the second dilator (e.g., its proximal end, or an index mark) it is suitably aligned to a part of the second dilator (e.g., an index marking on a scale). If an index scale is used, it may be on either or both of the first and second dilator. For the sake of description of the method, the distal ends of the first and second dilators are assumed to be aligned to one another in the aligned position; optionally, they are offset by some known amount. Additionally or alternatively, the insertion depth of the second dilator relative to the total vaginal length is used to longitudinally position and/or verify the position of the second dilator.

At this stage, the longitudinal positions of the distal ends of the first dilator and second dilator are both known relative to that of the rectouterine pouch wall which is to be dilated. Optionally, either dilator can be advanced or retracted relative to the other in any suitable sequence, and so long as the sequence of movements and their distances are tracked, their positions relative to the rectouterine pouch wall will remain known.

For example, at block 557, in some embodiments, the first dilator is advanced into the rectouterine pouch while the second dilator remains fixed (e.g., clamped). The relative motion is optionally monitored by looking at scale marking motions on the proximal ends of the dilators. At block 559, e.g., once the first dilator is sufficiently advanced (for example, 15 mm) to achieve a full first-stage dilation, the second dilator is advanced (e.g., until the original relative alignment of the two is restored). Additionally or alternatively, the changing insertion depths are controlled/monitored relative to the total vaginal length.

Additionally or alternatively (at blocks 558 and/or 560), advancing distance is controlled by making reference to the TVL determined at block 552.

From this position, at block 561, the first dilator (and trocar needle 207, if not yet withdrawn) may be removed; and the second dilator may remain as a longitudinal positioning reference for positioning the cannula 201 at block 563. Optionally, the cannula 201 has a handle which is long enough to support a scale and/or reference mark that aligns with some visible part of the second dilator (a scale mark, distal end, or indicator mark) when the cannula 201 is in place. Additionally or alternatively, the cannula insertion depth is controlled/monitored relative to the total vaginal length.

At block 565, the second dilator is removed. Cannula 201 is now positioned crossing the rectouterine wall, and at a known longitudinal depth relative to the rectouterine wall.

Optionally, the stepped dilator 1100 of FIGS. 11A-11E is used by this method, with the insertion of FIG. 6E optionally occurring in two stages, one for each of distal tapering region 1121, and proximal tapering region 1117, optionally with a pause between the two stages enabled by allowing the physician to sense a change in insertion resistance upon transitioning from distal tapering region 1121 to isolating region 1119.

Cannula Fixation and Robot Alignment to Cannula

Free-Positioned Alignment System

Reference is now made to FIGS. 9A-9D, which comprise views representing an instrument holder 900 for cannula 201 and its configuration for use, wherein instrument holder 900 includes a motor unit stopper 902 for use in setting an initial robotic arm position, according to some embodiments of the present disclosure.

FIG. 9A schematically shows an in instrument holder 900, comprising a mounting block 901 and a stopper arm 902. In some embodiments, stopper arm 902 is hinged upon hinge 904 to rotate to different orientations relative to mounting block 901.

FIG. 9B shows cannula 201 and associated handle 202 mounted to mounting block 901. Mounting, in some embodiments, comprises positioning a proximal end of handle 202 in a well-defined position relative to mounting block 901; for example, flush with an aperture 903 of a lumen within block 901 sized and shaped to receive handle 202. Fixation of cannula 201 relative to block 901 is optionally assured by tightening a tightening handle 905.

FIG. 9C shows an overall mounting arm assembly 910, comprising a table-mounting block 911 (configured, e.g., with clamps and tightening handles supporting firm attachment to a table or other stabilizing surface), and jointed arm 912 extending distally from the mounting block 911 to attachment at its distal side to mounting block 901.

FIG. 9D shows the instrument holder 900 with motor unit stopper 902 configured to set an initial working distance of motor unit 930. Motor unit stopper 902 is sized so that when positioned to horizontally protrude from block 901, its distal end marks the distance at which motor unit 930 should be set so that its arms (which themselves have a well-known predetermined length) reach a defined (and safe) initial distal-most position within cannula 201 (e.g., at the distal end of the cannula) when cannula 201 positioned relative to mounting block 901 as shown in FIG. 9B (the cannula is not shown in FIG. 9D). Robotic arms 305 (not seen) pass distally from motor unit 930 within extenders 920. Extenders 920 comprise tubes having a lumen sized to pass the robotic arms 305 thereinto, for example, a lumen of, for example, at least 7 mm, 8 mm, 9 mm, or 10 mm. Extenders 920 may be aligned (e.g., set within slots 921 of FIG. 9B) to guide the robotic arms 305 to cannula 201.

By appropriate positioning of its parts at marked and predetermined positions, a kit comprising cannula 201 and handle 202, and instrument holder 900 with motor unit stopper 902 (optionally including extenders 920 and/or motor unit 930 and associated arms 305) potentially helps to achieve a rapid, reproducible initial setup providing a well-determined initial relationship between the distal end of cannula 201, and the distal ends of robotic arms 305, for example, an alignment of the two ends.

To allow initiation of robotic arm movement in a distal direction, motor unit stopper 902 is allowed to swing away from the horizontal position (e.g., downward), so that motor unit 930 can advance distally without interference. Preferably, attachment of motor unit stopper 902 to block 901 is configured to allow conversion between a first position that prevents advance of motor unit 930, and a second position that allows it; without disturbing the position of structures on either side of it—for example, without disturbing positions of the cannula 201 or the motor unit 930. The attachment is not necessarily by a hinge (for example, stopper 902 may be telescoping, slideable within block 901, or otherwise moveable). A hinge provides a potential advantage by allowing a reproducible longitudinal stopper position to be obtained when the stopper is oriented in the horizontal (oriented to the longitudinal axis of the cannula) position, together with ready conversion to a non-stopping position without having to exert either longitudinal force to slide the stopper 902, or torque on a fastener to release the stopper 902.

Lock-Positioned Alignment System

Figure 12A:
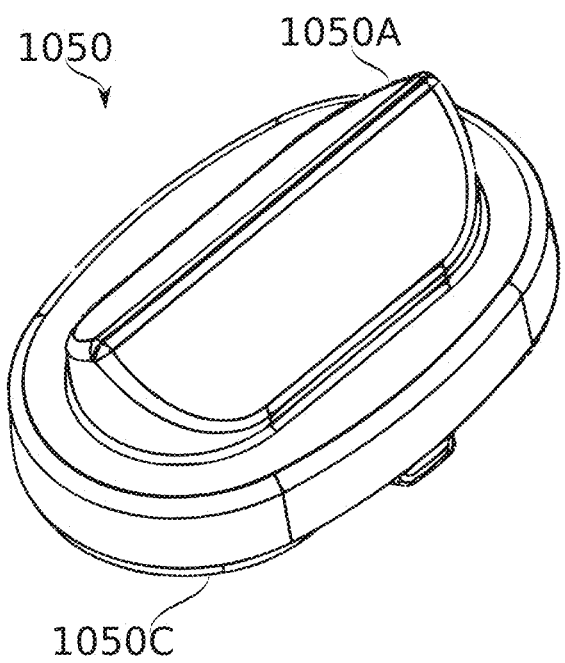
FIGS. 12A-12C schematically represent a duck-bill gasket used to seal access to the proximal aperture of an access device, according to some embodiments of the present disclosure.
Figure 12B:
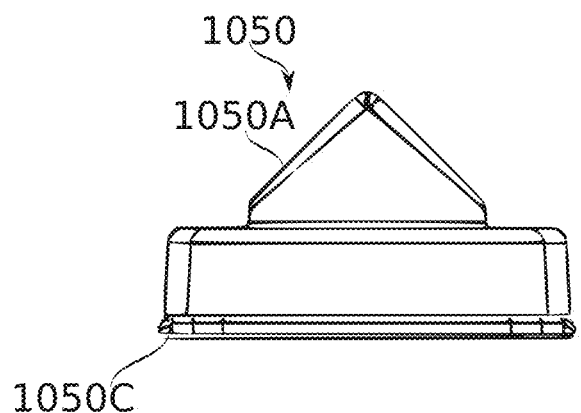
Figure 12C:
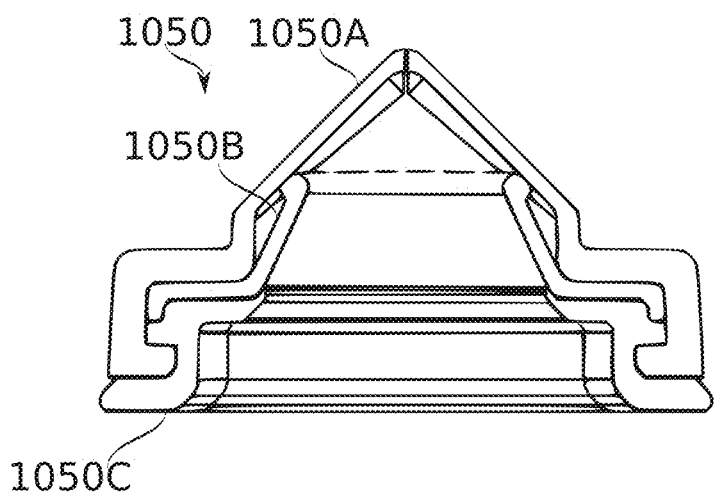

Reference is now made to FIGS. 10A-10E, which schematically illustrate views representing a collapsing instrument holder 1000 for cannula 1010 and its configuration for use in setting an initial robotic arm position relative to cannula 1010, according to some embodiments of the present disclosure. Reference is also made to FIGS. 10F-10J, which schematically represent components of collapsing instrument holder 1000, according to some embodiments of the present disclosure. Further reference is made to FIGS. 12A-12C, which schematically represent a duck-bill gasket 1050 used to seal access to the proximal aperture of access device 1001, according to some embodiments of the present disclosure.

FIG. 10A shows an access device 1001, shaped for insertion into a gel seal 1003 (in a position indicated, for example, in FIGS. 10B-10C). In use, gel seal 1003 is positioned at the vaginal entrance to provide protected access; thus, elements positioned to the right of gel seal 1003 would be positioned intra-vaginally during a procedure, and elements positioned to the left would be positioned extra-vaginally.

Trans-seal region 1001A of access device 1001 is flanged on either side, and seats within the gel membrane of gel seal 1003. External (proximal) side 1001B of access device 1001 (also referred to herein as a "trocar"), in some embodiments, is provided with a mounting projection 1002. Lumen 1004 of access device 1001 is sized to allow insertion of stepped dilator 1100 (e.g., as shown in FIG. 10B), or optionally another dilator/dilator system, for example, a two-piece dilator comprising inner dilator 205 and outer dilator 203. Also shown in FIG. 10B assembled together with stepped dilator 1100 are needle handle 511 of needle 207 and dilator handle 510.

Lumen 1004 of access device 1001 is also sized to allow insertion of a cannula 1010 over stepped dilator 1100 (or other dilatory system). When inserted to lumen 1004, in some embodiments, cannula 1010 is fittingly contained by access device 1001, and optionally locked thereto. Cannula 1010, in some embodiments, comprises a body with an elongated (e.g., oval) cross-section, having a slanted distal aperture 209, for example as described in relation to FIG. 3L, and a flange 221 at its proximal side. In some embodiments, flange 221 includes a receiving indentation for a ball stop 1006 provided on access device 1001 which controls relative motion between cannula 1010 and access device 1001 when locked.

In some embodiments, a two-seal "duck bill" gasket 1050 (shown in FIG. 10C, and FIGS. 12A-12C) is inserted into the proximal aperture of access device 1001 after positioning of cannula 1010. A first sealing member 1050A of gasket 1050 is normally sealed (two opposite sides pushed together) when there is nothing inserted into cannula 1010. Upon insertion of robotic arm guide 1032 (explained further in relation to FIGS. 10D-10E), first sealing member 1050A is forced open, while a second sealing member 1050B, which is normally open, is shaped so that it seals around the robotic arm guide 1032. The sealing members 1050A, 1050B are made of a soft elastic material, for example, a silicone rubber. In some embodiments, gasket body 1050C comprises a rigid polymer or metal material that provides support to sealing members 1050A, 1050B to help maintain the overall shape of gasket 1050. In some embodiments, each of the sealing members 1050A, 1050B is shaped so that it has a long axis and a short axis, with the long axis being at least twice as long as the short axis.

The placement of the above-described elements generally corresponds, in some embodiments, to the operations of block 120 (dilate and introduce cannula) and block 122 (sealing unit) of FIG. 3J.

Fixation corresponding to operation of block 124 of FIG. 3J, in some embodiments, comprises attaching mounting projection 1002 to mounting block 1020. Mounting block 1020 may itself be affixed, for example, to a platform stationary relative to the patient, such as an operating table. In some embodiments, attachment comprises insertion of mounting projection 1002 into a receiving aperture 1061 (shown in FIG. 10J) of mounting block 1020. In some embodiments, notch 1005 or another shape on mounting projection 1002 engages to a lock within receiving aperture 1061. Optionally, button 1021 is pressed to assist and/or activate engagement and/or release of mounting projection 1002 from the lock.

Mounting block 1020 is a component of instrument holder 1000. Attached to mounting block 1020, instrument holder 1000 additionally comprises spacing arm 1024 and aligning arm 1030. In some embodiments, spacing arm 1024 is attached to mounting block 1020 by stopped hinge 1022, and aligning arm 1030 is in turn attached to spacing arm 1024 by stopped hinge 1028. In some embodiments, spacing arm 1024 is telescoping (reversibly extendible and retractable). Optionally, release and/or locking of telescoping is controlled by a button 1026 or other control member.

Figure 10D:
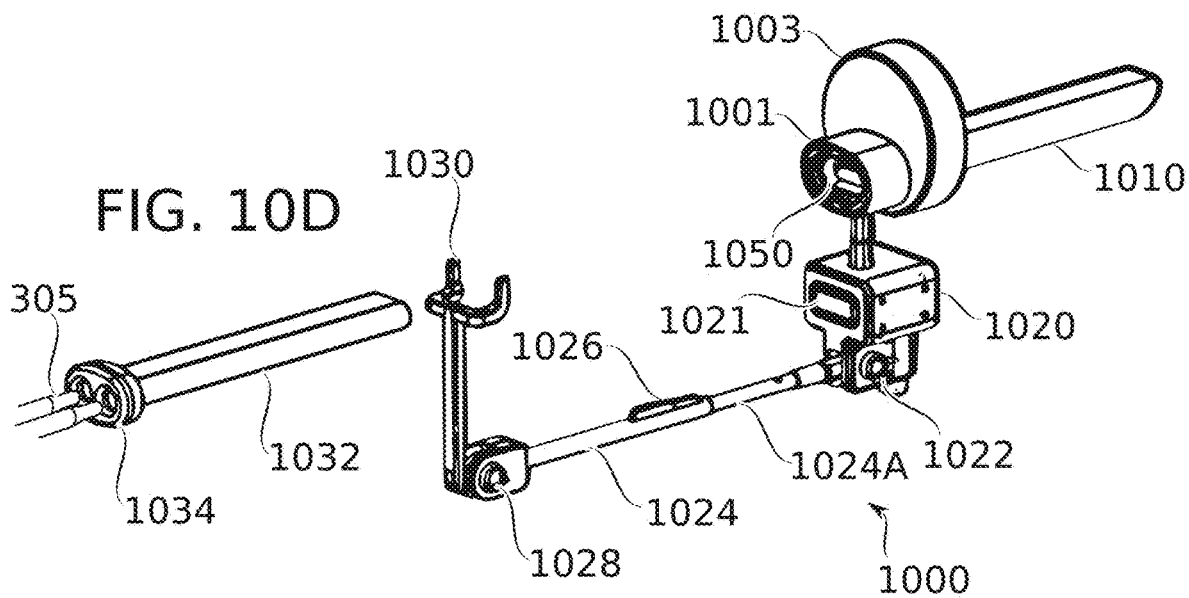
Figure 10E:
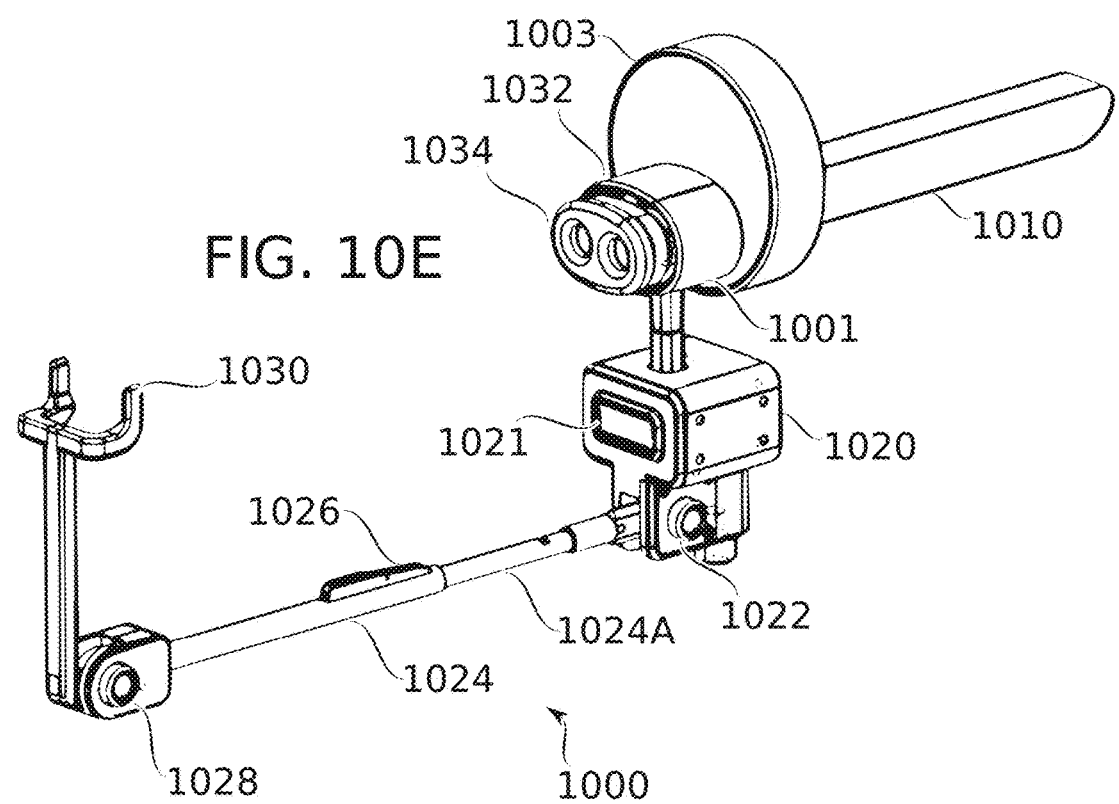

The use of stopped hinges 1022, 1028 and button 1026 to position spacing arm 1024 and aligning arm 1030 are further illustrated in FIGS. 10D-10E.

In some embodiments of the invention, cannula 1010 is used to provide intraperitoneal access to one or more robotic arms, for example robotic arms 305 as described, for example, in relation to FIGS. 3I and 7A-7B. As also described in the Overview herein, it is a potential advantage to be able to position these robotic arms so that they begin at a well-known distance of longitudinal advance through cannula 1010, and at a well-known angle of approach (generally an angle of approach axially aligned with cannula 1010).

In FIGS. 10D-10E, spacing arm 1024 and aligning arm 1030 comprise an assembly shown fully deployed (in a deployed position) in order to help set a starting position for robotic arms being introduced into cannula 1010. In some embodiments, this comprises:

Rotating spacing arm 1024 90° from its vertically downward stowed position (seen in FIG. 10C) to a horizontal deployment position.

Extending spacing arm 1024 to set the spacing distance by pressing on button 1026, and pulling to expose telescoping arm portion 1024A.

Rotating aligning arm 1030 from its stowed position against spacing arm 1024 (as in FIG. 10C) to a vertical deployment position.

Optionally, spacing arm 1024 and aligning arm 1030 are returned to their stowed positions after use to position robotic arms correctly. A potential advantage of post-use stowing is so that they do not interfere with further movements of the robotic arms (e.g., advancing deeper into the intraperitoneal cavity).

FIGS. 10F-10J illustrate these components in more detail. FIGS. 10F-10H show spacing arm 1024 in a collapsed (unextended) configuration. Stopped hinges 1022, 1028 can be seen, including details of an optional embodiment thereof. For example, in the case of stopped hinge 1022, each of (optionally four) projections 1063 is spaced around a circumference of stopped hinge 1022. Each projection 1063 extends into a respective notch of plate 1022A. The projections 1063 are fixed to the orientation of block 1020 (FIG. 10J), while plate 1022A is affixed to spacing arm 1024. Accordingly, as long as the projections 1063 engage the notches of plate 1022A, spacing arm 1024 is fixed in orientation. Upon actuating button 1062, projections 1063 are recessed out of their notches, allowing spacing arm 1024 to rotate freely. Optionally, the projections 1063 are held in place by plate 1022A once the notches are moved out of alignment with them, so that button 1022A can be released while spacing arm 1024 continues to move freely.

Once spacing arm 1024 is deployed by a full 90°, the notches of plate 1022A and projections 1063 come back into alignment, allowing projections 1063 to spring back into place, locking spacing arm 1024 in a new orientation. This mechanism has potential advantages of (1) only allowing one deployed orientation of spacing arm 1024, and (2) being strong enough to hold the horizontally deployed weight of spacing arm 1024 and aligning arm 1030 without collapsing.

Stopped hinge 1028, in some embodiments, comprises a similar mechanism, comprising projections 1065, button 1067, and notched plate 1066. Notched plate 1066 is again affixed to spacing arm 1024, while the projections 1065 are fixed to the orientation of aligning arm 1030.

In the fully deployed position of FIGS. 10D-10E, horizontal bar 1068 (FIG. 10I) of aligning arm 1030 acts to set an elevation across which robotic arms should be horizontally passed while aiming at cannula 1010 in order to be level with the longitudinal axis of cannula 1010. Similarly, the robotic arms should pass through the space between vertical bars 1064 in order to approach cannula 1010 along its central longitudinal axis. Furthermore, in some embodiments, a motor unit or other housing holding a robotic arm which is being positioned is in position when some designated portion of it (a "stopper-receiving portion") is pressed up against a portion of aligning arm 1030 that acts as a stopper, for example, pressed against the vertically extending main bar 1069 of aligning arm 1030.

Returning now to FIGS. 10D-10E: in some embodiments, robotic arms 305 are sheathed (e.g., two round arms side-by-side) using arm sheath 1032 before being passed into cannula 1010 (e.g., in performing the operations of block 126 of FIG. 3J). In some embodiments, arm sheath 1032 has an inner lumen sized to allow at least two robotic arms having a minimum outer diameter of about 8.6 mm to pass therethrough. In some embodiments, for example, a minimum diameter of the inner lumen of arm sheath 1032 is about 9 mm, 10 mm, or 11 mm.

A potential advantage of sheath 1032 is to ensure that the arms are straight, and moreover to ensure that no part of them will be accidentally snagged during passage into and through cannula 1010. In some embodiments, moreover, there is provided a gasket 1034, comprising a fitted hole for each of two robotic arms that may be passed therethrough. Gasket 1034 fittingly attaches to a proximal end of arm sheath 1032, to act as another protective seal. Optionally, arm sheath 1032 is constructed from stainless steel. Optionally gasket 1034 is manufactured from a flexible polymer such as a silicone rubber.

Stepped Dilator

Reference is now made to FIGS. 11A-11E, which schematically represent a stepped dilator 1100, dilator handle 510, and trocar needle 207, according to some embodiments of the present disclosure. Reference Dilator handle 510 and trocar needle 207 are, in some embodiments, substantially as described, for example, in relation to FIGS. 5D-5F, 5H, 5I, and 5K.

In some embodiments, stepped dilator 1100 comprises, along a distal working end 1115 of a single dilator, distal and proximal tapering regions 1121 and 1117 (FIGS. 11B, 11C). Distal and proximal tapering regions 1121, 1117 are, in some embodiments, substantially shaped as described for embodiments of tapering regions 213 and 218 of the two-dilator combination which is described herein, for example, in relation to FIGS. 2A-3I and 5K. Nevertheless, some specific details of tapering region shapes are repeated here for clarity.

In some embodiments, distal (first) tapering region 1121 has a blunted distal-most portion. The distal-most portion optionally has a port through which a trocar needle 207 can be extended. Optionally, the distal-most portion curves proximally, widening in both width and height through a radius of about 2.5 mm, then expanding primarily in width to form a wide oblong cross-section about 15 mm proximal to the distal-most portion (or another distance, for example in the range of about 10-20 mm).

In some embodiments, a non-dilating isolating region 1119 extends longitudinally between the distal and proximal tapering regions. Preferably, isolating region 1119 is long enough to allow an inserting physician to sense a reduction in insertion resistance upon passing the proximal side of distal tapering region 1121, and reduce insertion force in response, so that dilation is paused. This distance is optionally in the range of about 5-15 mm. In some embodiments, isolating region 1119 is of a constant cross-section extending proximally from the distal side of isolating region 1119 until reaching the distal side of proximal tapering region 1117. Alternatively, isolating region 1119A (FIG. 11C), in some embodiments, comprises a constriction (e.g., a tapering constriction) relative to the proximal-side cross-section of distal tapering region 1121, which potentially acts as a detente that accentuates for a physician the sensation of reduced insertion resistance. The constriction may also allow a physician to detect by feel a difference between an initial dilation after which the dilated tissue perimeter retains elasticity (tending to re-collapse the dilated opening), and a dilation where a tear has been induced, potentially reducing the tendency of the dilated opening to exert inward force on the dilator.

In some embodiments, proximal (second) tapering region 1117 has a distal-most cross-section arising from the proximal-most portion of isolating region 1119. From there, the second dilator's cross-section expands going proximally for about 15 mm (or another distance, for example in the range of about 10-20 mm). The maximum of the further expansion is an expansion by about, for example, about 5 mm, 7.5, mm, 10 mm, or 12.5 mm. Optionally, there is a larger expansion along one axis of the incision cross-section than along another axis; for example, there may be a relative factor of expansion of about 1:1.5, 1:2, or 1:3.

In some embodiments, a body 1111 of dilator 1100 is constructed of a sterilizable and re-sterilizable (e.g., autoclave compatible) material, e.g. stainless steel. Optionally, an inset region 1113 is provided on one or both sides of body 1111. This potentially reduces weight of dilator 1100 (e.g., in embodiments where body 1111 is constructed of a solid piece of metal).

In some embodiments, dilator 1100 is at least 17 cm in overall length without handle 510. In some embodiments, threaded region 1102A is threaded to accept a thread of handle 510. Handle 510 is optionally at least 20 cm long.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this disclosure may be presented with reference to a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features, which are, for clarity, described in the context of separate embodiments within the present disclosure, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

What is claimed is:

1. A kit for setting a position of a robotic arm system along a longitudinal axis of a cannula inserted to a body orifice, wherein the robotic arm system comprises a motor unit and at least one robotic arm extending, when positioned, distally from the motor unit along the longitudinal axis, the motor unit and the at least one robotic arm extending distally from the motor unit to a predetermined distance from a stopper-receiving portion of the motor unit; the kit comprising:
    the cannula, including a cannula body configured for insertion to the body orifice;
    a mounting block, configured for attachment to the cannula; and
    an assembly attached to the mounting block and comprising a spacing arm and an aligning arm, and movable between a stowed position and a deployed position;
    wherein the deployed position of the assembly places elements of the aligning arm where they indicate a predetermined position along the longitudinal axis;
    wherein a distal end of the at least one robotic arm aligns with a distal end of the cannula when the at least one robotic arm is inserted to the cannula, and a stopper portion of the aligning arm contacts the stopper-receiving portion of the motor unit to prevent longitudinal advance of the motor unit.

2. The kit of claim 1, wherein the mounting block attaches to the cannula by connecting to an access device having a lumen sized to fittingly accept the cannula therewithin.

3. The kit of claim 1, wherein the spacing arm and the aligning arm deploy by hinging around a plurality of stopped hinges, each stopped hinge defining at least a stopped deployed position, and a stopped stowed position.

4. The kit of claim 3, wherein each stopped hinge comprises a plurality of projections and respective notches; wherein moving said projections out of said respective notches allows said spacing arm to rotate freely.

5. The kit of claim 1, comprising an arm sheath with a lumen sized to accept the at least one robotic arm, and an outer surface sized to fit within the cannula.

6. The kit of claim 5, further comprising a gasket attached to a proximal end of said arm sheath, the gasket comprising a fitted hole for said at least one robotic arm to be passed therethrough.

7. The kit of claim 1, wherein a transverse cross-section of an inner lumen of the cannula transverse to the longitudinal axis of the cannula has a long axis long enough to allow simultaneous insertion of at least two cylindrical members, each at least 8 mm in diameter.

8. The kit of claim 1, wherein the cannula comprises a distal aperture which is slanted relative to the longitudinal axis of the cannula.

9. The kit of claim 1, wherein the cannula is constructed from stainless steel.

10. The kit of claim 1, wherein said cannula is sized for transvaginal insertion.

11. The kit of claim 1, wherein said spacing arm is telescoping.

12. The kit of claim 11, comprising a control button for releasing and/or locking of said telescoping spacing arm.

13. A kit for setting a position of a robotic arm system along a longitudinal axis of a cannula inserted to a body orifice, wherein the robotic arm system comprises a motor unit and at least one robotic arm extending, when positioned, distally from the motor unit along the longitudinal axis, the kit comprising:
    the cannula, including a cannula body configured for insertion to the body orifice;
    a mounting block, configured for attachment to the cannula; and
    an assembly attached to the mounting block and comprising a spacing arm and an aligning arm, and movable between a stowed position and a deployed position;
    wherein the deployed position of the assembly places elements of the aligning arm where they indicate a predetermined position along the longitudinal axis;
    wherein the spacing arm and the aligning arm deploy by hinging around a plurality of stopped hinges, each stopped hinge defining at least a stopped deployed position, and a stopped stowed position; wherein each stopped hinge comprises a plurality of projections and respective notches; wherein moving said projections out of said respective notches allows said spacing arm to rotate freely.

14. The kit of claim 13, wherein the mounting block attaches to the cannula by connecting to an access device having a lumen sized to fittingly accept the cannula therewithin.

15. The kit of claim 13, wherein the motor unit and the at least one robotic arm extend distally from the motor unit to a predetermined distance from a stopper-receiving portion of the motor unit;

wherein a distal end of the at least one robotic arm aligns with a distal end of the cannula when the at least one robotic arm is inserted to the cannula, and a stopper portion of the aligning arm contacts the stopper-receiving portion of the motor unit to prevent longitudinal advance of the motor unit.

16. The kit of claim 13, comprising an arm sheath with a lumen sized to accept the at least one robotic arm, and an outer surface sized to fit within the cannula.

17. The kit of claim 16, further comprising a gasket attached to a proximal end of said arm sheath, the gasket comprising a fitted hole for said at least one robotic arm to be passed therethrough.

18. The kit of claim 13, wherein a transverse cross-section of an inner lumen of the cannula transverse to a longitudinal axis of the cannula has a long axis long enough to allow simultaneous insertion of at least two cylindrical members, each at least 8 mm in diameter.

19. The kit of claim 13, wherein the cannula comprises a distal aperture which is slanted relative to the longitudinal axis of the cannula.

20. The kit of claim 13, wherein the cannula is constructed from stainless steel.

21. The kit of claim 13, wherein said cannula is sized for transvaginal insertion.

22. The kit of claim 13, wherein said spacing arm is telescoping.

23. The kit of claim 22, comprising a control button for releasing and/or locking of said telescoping spacing arm.

* * * * *